(12) United States Patent
Humphrey

(10) Patent No.: US 10,433,969 B2
(45) Date of Patent: *Oct. 8, 2019

(54) ARTHROPLASTY IMPLANTS AND METHODS FOR ORIENTING JOINT PROSTHESIS

(71) Applicant: DELTOID, LLC, Eagle, ID (US)

(72) Inventor: C. Scott Humphrey, Eagle, ID (US)

(73) Assignee: United Orthopedic Corp. (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/941,861

(22) Filed: Mar. 30, 2018

(65) Prior Publication Data
US 2018/0221160 A1    Aug. 9, 2018

Related U.S. Application Data

(63) Continuation-in-part of application No. 14/586,677, filed on Dec. 30, 2014, now Pat. No. 9,956,083, and (Continued)

(51) Int. Cl.
*A61F 2/40* (2006.01)
*A61F 2/30* (2006.01)

(52) U.S. Cl.
CPC ........ *A61F 2/4014* (2013.01); *A61F 2/30771* (2013.01); *A61F 2002/3093* (2013.01); (Continued)

(58) Field of Classification Search
CPC ........ A61F 2/40; A61F 2/4014; A61F 2/4003; A61F 2/4081; A61F 2002/4018
See application file for complete search history.

(56) References Cited

U.S. PATENT DOCUMENTS 3,891,998 A    7/1975 Lennox
4,231,120 A    11/1980 Day
(Continued)

FOREIGN PATENT DOCUMENTS

EP    2604226 A1    6/2013
EP    2689750 A1    1/2014
(Continued)

OTHER PUBLICATIONS http://www.lima.it/repository/fck/image/Lima.
(Continued)

*Primary Examiner* — Jason-Dennis N Stewart
(74) *Attorney, Agent, or Firm* — McNees Wallace & Nurick LLC

(57) ABSTRACT

A system for long bone arthroplasty includes humeral head prosthesis components, and an array of humeral head prosthesis components, each humeral head prosthesis component in the array having a convex articulation surface that is hemi-elliptical and defined by a major axis, a minor axis, an apex, and a base having an elliptical cross sectional shape defined by a major diameter along the major axis and a minor diameter along the minor axis, wherein the array of elliptical humeral head prosthesis components provides for suitable and sufficient anatomical fit within a variation of up to and not more than 3 mm in at least 96% of a patient population, and up to 99% of a patient population.

20 Claims, 21 Drawing Sheets

Related U.S. Application Data a continuation-in-part of application No. 15/263,012, filed on Sep. 12, 2016, now Pat. No. 9,962,266.

(60) Provisional application No. 62/490,395, filed on Apr. 26, 2017, provisional application No. 62/217,695, filed on Sep. 11, 2015, provisional application No. 62/217,703, filed on Sep. 11, 2015, provisional application No. 61/928,399, filed on Jan. 16, 2014, provisional application No. 61/921,593, filed on Dec. 30, 2013.

(52) U.S. Cl.
CPC ............. *A61F 2002/30253* (2013.01); *A61F 2002/30331* (2013.01); *A61F 2002/30332* (2013.01); *A61F 2002/30616* (2013.01); *A61F 2002/30934* (2013.01); *A61F 2002/4022* (2013.01); *A61F 2002/4051* (2013.01)

(56) References Cited

U.S. PATENT DOCUMENTS

| | | |
|---|---|---|
| D258,968 S | 4/1981 | Adler |
| 4,261,062 A | 4/1981 | Amstutz et al. |
| D285,969 S | 9/1986 | Kinnett |
| 4,865,605 A | 9/1989 | Dines et al. |
| 4,919,670 A | 4/1990 | Dale et al. |
| 4,964,865 A | 10/1990 | Burkhead et al. |
| 5,032,132 A | 7/1991 | Matsen, III et al. |
| 5,080,673 A | 1/1992 | Burkhead et al. |
| 5,370,703 A | 12/1994 | Willert et al. |
| 5,383,936 A | 1/1995 | Kubein-Meesenburg et al. |
| 5,489,309 A | 2/1996 | Lackey et al. |
| 5,593,448 A | 1/1997 | Dong |
| 5,702,447 A | 12/1997 | Walch et al. |
| 5,702,457 A | 12/1997 | Walch et al. |
| 5,723,018 A | 3/1998 | Cyprien et al. |
| 5,800,551 A | 9/1998 | Williamson et al. |
| 6,187,050 B1 | 2/2001 | Khalili et al. |
| 6,197,062 B1 | 3/2001 | Fenlin |
| 6,228,119 B1 | 5/2001 | Ondrla et al. |
| 6,364,910 B1 | 4/2002 | Shultz et al. |
| 6,368,353 B1 | 4/2002 | Arcand |
| 6,379,386 B1 | 4/2002 | Resch et al. |
| 6,406,495 B1 | 6/2002 | Schoch |
| 6,508,840 B1 | 1/2003 | Rockwood, Jr. et al. |
| 6,514,287 B2 | 2/2003 | Ondrla et al. |
| 6,537,321 B1 | 3/2003 | Horber |
| 6,673,115 B2 | 1/2004 | Resch et al. |
| 6,679,916 B1 | 1/2004 | Frankle et al. |
| 6,699,289 B2 | 3/2004 | Iannotti et al. |
| 6,719,799 B1 | 4/2004 | Kropf |
| 6,783,549 B1 | 8/2004 | Stone et al. |
| 6,790,234 B1 | 9/2004 | Frankle |
| 6,911,047 B2 | 6/2005 | Rockwood, Jr. et al. |
| 6,942,699 B2 | 9/2005 | Stone et al. |
| 6,953,478 B2 | 10/2005 | Bouttens et al. |
| 7,044,973 B2 | 5/2006 | Rockwood, Jr. et al. |
| 7,160,328 B2 | 1/2007 | Rockwood, Jr. et al. |
| 7,175,663 B1 | 2/2007 | Stone |
| 7,329,284 B2 | 2/2008 | Maroney et al. |
| 7,462,197 B2 | 12/2008 | Tornier et al. |
| 7,470,287 B2 | 12/2008 | Tornier et al. |
| 7,604,665 B2 | 10/2009 | Iannotti et al. |
| 7,621,961 B2 | 11/2009 | Stone |
| 7,648,530 B2 | 1/2010 | Habermeyer et al. |
| 7,753,959 B2 | 7/2010 | Berelsman et al. |
| 7,819,923 B2 | 10/2010 | Stone et al. |
| 7,854,768 B2 | 12/2010 | Wiley et al. |
| 7,879,275 B2 | 2/2011 | Smith et al. |
| 7,892,287 B2 | 2/2011 | Deffenbaugh |
| 7,922,769 B2 | 4/2011 | Deffenbaugh et al. |
| 7,959,680 B2 | 6/2011 | Stone et al. |
| 7,981,161 B2 | 7/2011 | Choi et al. |
| 8,007,538 B2 | 8/2011 | Gunther |
| 8,014,984 B2 | 9/2011 | Iannotti et al. |
| 8,038,719 B2 | 10/2011 | Gunther |
| 8,048,161 B2 | 11/2011 | Guederian et al. |
| 8,062,376 B2 | 11/2011 | Shultz et al. |
| 8,070,820 B2 | 12/2011 | Winslow et al. |
| 8,080,063 B2 | 12/2011 | Ferrand et al. |
| 8,182,542 B2 | 5/2012 | Ferko |
| 8,236,059 B2 | 8/2012 | Stone et al. |
| 8,246,687 B2 | 8/2012 | Katrana et al. |
| 8,287,600 B2 | 10/2012 | Angibaud |
| 8,317,871 B2 | 11/2012 | Stone et al. |
| 8,380,471 B2 | 2/2013 | Iannotti et al. |
| 8,419,798 B2 | 4/2013 | Ondrla et al. |
| 8,425,614 B2 | 4/2013 | Winslow et al. |
| 8,449,617 B1 | 5/2013 | McDaniel et al. |
| 8,454,702 B2 | 6/2013 | Smits et al. |
| 8,480,750 B2 | 7/2013 | Long |
| 8,506,638 B2 | 8/2013 | Vanasse et al. |
| 8,512,410 B2 | 8/2013 | Metcalfe et al. |
| 8,529,629 B2 | 9/2013 | Angibaud et al. |
| 8,545,511 B2 | 10/2013 | Splieth et al. |
| 8,556,980 B2 | 10/2013 | Deffenbaugh |
| 8,608,805 B2 | 12/2013 | Forrer et al. |
| 8,632,598 B2 | 1/2014 | McDaniel et al. |
| 8,663,335 B2 | 3/2014 | Katrana et al. |
| 8,673,015 B2 | 3/2014 | Maroney et al. |
| 8,690,952 B2 | 4/2014 | Dallmann |
| 8,696,677 B2 | 4/2014 | Chavarria et al. |
| 8,702,804 B2 | 4/2014 | Smith et al. |
| 8,721,726 B2 | 5/2014 | Capon et al. |
| 8,721,727 B2 | 5/2014 | Ratron et al. |
| 8,721,728 B2 | 5/2014 | Winslow et al. |
| 8,778,028 B2 | 7/2014 | Gunther et al. |
| 8,845,742 B2 | 9/2014 | Kusogullari et al. |
| 8,845,750 B2 | 9/2014 | Slavitt |
| 8,876,907 B2 | 11/2014 | Baptista et al. |
| 8,882,845 B2 | 11/2014 | Wirth et al. |
| 8,920,508 B2 | 12/2014 | Iannotti et al. |
| 8,932,361 B2 | 1/2015 | Tornier et al. |
| 9,474,619 B2 | 10/2016 | Reubelt et al. |
| 9,512,445 B2 | 12/2016 | Iannotti |
| 2001/0011192 A1 | 8/2001 | Ondrla et al. |
| 2001/0037153 A1 | 11/2001 | Rockwood, Jr. et al. |
| 2002/0082702 A1 | 6/2002 | Resch et al. |
| 2003/0097183 A1 | 5/2003 | Rauscher et al. |
| 2003/0114933 A1 | 6/2003 | Bouttens et al. |
| 2003/0125809 A1 | 7/2003 | Iannotti et al. |
| 2004/0059424 A1 | 3/2004 | Guederian et al. |
| 2004/0064189 A1 | 4/2004 | Maroney et al. |
| 2004/0225367 A1 | 11/2004 | Glien et al. |
| 2005/0060039 A1 | 3/2005 | Cyprien |
| 2005/0107882 A1 | 5/2005 | Stone et al. |
| 2005/0209700 A1 | 9/2005 | Rockwood, Jr. et al. |
| 2005/0261775 A1 | 11/2005 | Baum et al. |
| 2005/0288791 A1 | 12/2005 | Tornier et al. |
| 2006/0009852 A1 | 1/2006 | Winslow et al. |
| 2006/0069444 A1 | 3/2006 | Deffenbaugh |
| 2006/0079963 A1 | 4/2006 | Hansen |
| 2006/0111787 A1 | 5/2006 | Bailie et al. |
| 2006/0195194 A1 | 8/2006 | Gunther |
| 2007/0016304 A1 | 1/2007 | Chudik |
| 2007/0055380 A1 | 3/2007 | Berelsman et al. |
| 2007/0142917 A1 | 6/2007 | Roche et al. |
| 2007/0179624 A1 | 8/2007 | Stone et al. |
| 2007/0198094 A1 | 8/2007 | Berelsman et al. |
| 2007/0219637 A1 | 9/2007 | Berelsman et al. |
| 2007/0225818 A1 | 9/2007 | Reubelt et al. |
| 2007/0225821 A1 | 9/2007 | Reubelt et al. |
| 2007/0244564 A1 | 10/2007 | Ferrand et al. |
| 2008/0140211 A1 | 6/2008 | Doubler et al. |
| 2009/0062923 A1 | 3/2009 | Swanson |
| 2009/0125113 A1 | 5/2009 | Guederian et al. |
| 2009/0149961 A1 | 6/2009 | Dallmann |
| 2010/0016975 A1 | 1/2010 | Iannotti et al. |
| 2010/0087876 A1 | 4/2010 | Gunther |
| 2010/0087877 A1 | 4/2010 | Gunther |
| 2010/0087927 A1 | 4/2010 | Roche et al. |
| 2010/0145393 A1 | 6/2010 | Fallin et al. |

(56) References Cited

U.S. PATENT DOCUMENTS

| | | |
|---|---|---|
| 2010/0211183 A1 | 8/2010 | Chi |
| 2010/0228352 A1 | 9/2010 | Courtney, Jr. et al. |
| 2010/0249938 A1 | 9/2010 | Gunther et al. |
| 2010/0274359 A1 | 10/2010 | Brunnarius et al. |
| 2011/0035013 A1 | 2/2011 | Winslow et al. |
| 2011/0035018 A1 | 2/2011 | Deffenbaugh et al. |
| 2011/0054625 A1 | 3/2011 | Ferko et al. |
| 2011/0112648 A1 | 5/2011 | Gunther |
| 2011/0118846 A1 | 5/2011 | Katrana et al. |
| 2011/0125273 A1 | 5/2011 | Ratron et al. |
| 2011/0144758 A1 | 6/2011 | Deffenbaugh |
| 2011/0178603 A1 | 7/2011 | Long |
| 2011/0276144 A1 | 11/2011 | Wirth et al. |
| 2012/0029647 A1 | 2/2012 | Winslow et al. |
| 2012/0089233 A1 | 4/2012 | Capon et al. |
| 2012/0109321 A1 | 5/2012 | Stone et al. |
| 2012/0130498 A1 | 5/2012 | Long |
| 2012/0130499 A1 | 5/2012 | Long |
| 2012/0179262 A1 | 7/2012 | Metcalfe et al. |
| 2012/0209392 A1 | 8/2012 | Angibaud et al. |
| 2012/0221111 A1 | 8/2012 | Burkhead, Jr. et al. |
| 2012/0232667 A1 | 9/2012 | Katrana et al. |
| 2012/0239051 A1 | 9/2012 | De Wilde et al. |
| 2012/0253467 A1 | 10/2012 | Frankle |
| 2012/0277880 A1 | 11/2012 | Winslow et al. |
| 2012/0296439 A1 | 11/2012 | Slavitt |
| 2013/0060341 A1 | 3/2013 | Tornier et al. |
| 2013/0066433 A1 | 3/2013 | Veronesi et al. |
| 2013/0090736 A1 | 4/2013 | Katrana et al. |
| 2013/0090737 A1 | 4/2013 | Flaherty et al. |
| 2013/0123929 A1 | 5/2013 | McDaniel et al. |
| 2013/0166033 A1 | 6/2013 | Gunther |
| 2013/0173007 A1 | 7/2013 | Duport |
| 2013/0178943 A1 | 7/2013 | Duport |
| 2013/0190881 A1 | 7/2013 | Winslow et al. |
| 2013/0197651 A1 | 8/2013 | McDaniel et al. |
| 2013/0245775 A1 | 9/2013 | Metcalfe |
| 2013/0261629 A1 | 10/2013 | Anthony et al. |
| 2013/0261750 A1 | 10/2013 | Lappin |
| 2013/0261755 A1 | 10/2013 | Anthony et al. |
| 2013/0297030 A1 | 11/2013 | Katrana |
| 2013/0325131 A1 | 12/2013 | Roche et al. |
| 2013/0333187 A1 | 12/2013 | Long |
| 2014/0005789 A1 | 1/2014 | Chavarria et al. |
| 2014/0025173 A1 | 1/2014 | Cardon et al. |
| 2014/0031945 A1 | 1/2014 | Baptista et al. |
| 2014/0128983 A1 | 5/2014 | Flaherty et al. |
| 2014/0180425 A1 | 6/2014 | Katrana et al. |
| 2014/0214170 A1 | 7/2014 | Ratron et al. |
| 2014/0236304 A1 | 8/2014 | Hodorek et al. |
| 2014/0249638 A1 | 9/2014 | Winslow et al. |
| 2014/0277520 A1 | 9/2014 | Chavarria et al. |
| 2015/0012103 A1 | 1/2015 | Winslow et al. |
| 2015/0025641 A1 | 1/2015 | Masson |
| 2015/0025642 A1 | 1/2015 | Wirth et al. |

FOREIGN PATENT DOCUMENTS

| | | |
|---|---|---|
| EP | 2672929 A4 | 1/2018 |
| WO | WO03005933 A2 | 1/2003 |
| WO | WO03005933 A3 | 1/2003 |
| WO | WO2011073169 A1 | 6/2011 |
| WO | WO2012109245 A2 | 8/2012 |
| WO | WO2012125704 A2 | 9/2012 |
| WO | WO2013148229 A1 | 10/2013 |

OTHER PUBLICATIONS

Anatomical Shoulder System by Zimmer (Product Materials).

DePuy Brochure, Global Advantage Shoulder Arthroplasty System, 2000.

Tornier Affiniti Brochure, The Affiniti Total Shoulder Prosthesis, 2008.

Edwards, Bradley T., MD, et al., Radiographic comparison of pegged and keeled glenoid components using modern cementing techniques: A prospective randomized study, Journal of Shoulder and Elbow Surgery, Elsevier 2010, 251-257, Texas.

Amstutz, Harlan C., et al., UCLA Anatomic Total Shoulder Arthroplasty, Division of Orthopaedic Surgery, UCLA Medical School, Mar. 17, 1980, Los Angeles, CA.

Iannotti, Joseph R, M.D., et al., The Normal Glenohumeral Relationships, An Anatomical Study of One Hundred and Forty Shoulders, Department of Orthopaedic Surgery, University of Pennsylvania, Apr. 1992, vol. 74-A, No. 4, Pennsylvania.

Boileau, P., et al., The Three-Dimensional Geometry of the Proximal Humerus, Implications for Surgical Technique and Prosthetic Design, Department of Orthopaedic Surgery, 1997 British Editorial Society of Bone and Joint Surgery, vol. 79-B, Sep. 5, 1997, Nice and Lyon, France.

Hertel, Ralph, M.D., et al., Geometry of the Proximal Humerus and Implications for Prosthetic Design, Department of Orthopaedic Surgery, Inselspital, University of Berne, Switzerland, 2002.

Harrold, Fraser, M.D., PhD, et al., Humeral Head Arthroplasty and its Ability to Restore Original Humeral Head Geometry, Department of Orthopaedic and Trauma Surgery, Journal of Shoulder and Elbow Surgery, 2013, 115-121, Elsevier, Scotland, UK, 2013.

Jun, Bong Jae, PhD, et al., The Effects of Prosthetic Humeral Head Shape on Glenohumeral Joint Kinematics: A Comparison of Non-Spherical and Spherical Prosthetic Heads to the Native Head, Journal of Shoulder and Elbow Surgery, 2013, 1423-1432, Elsevier, Cleveland, Ohio.

FIG 2
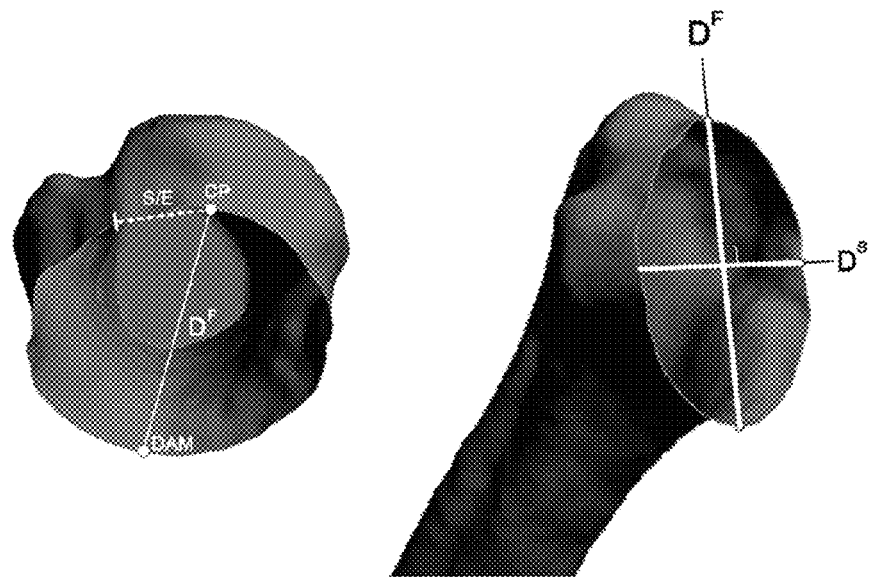
Ellipital Head Formulae
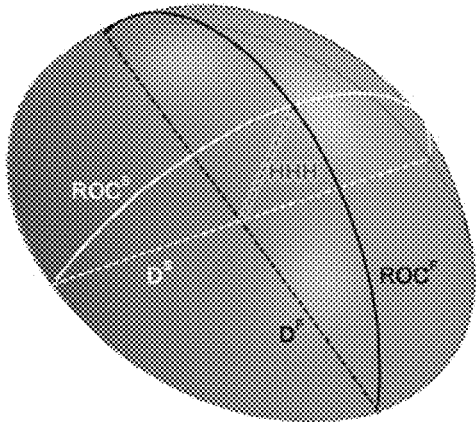
For a given length (mm) of $D^F$:
$D^S = 0.69(D^F) + 10.8$
$HHH = 0.30(D^F) + 3.2$
$ROC^F = 0.53(D^F) - 0.5$, and
$ROC^S = 0.44(D^F) + 2.2$
Spherical Head Formulae
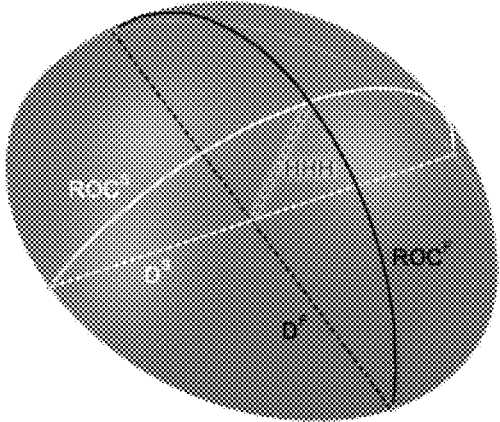
For a given length (mm) of $D^F$:
$D^S = D^F$
$HHH = 0.30(D^F) + 3.2$
$ROC^F = 0.53(D^F) - 0.5$, and
$ROC^S = ROC^F$ FIG 8
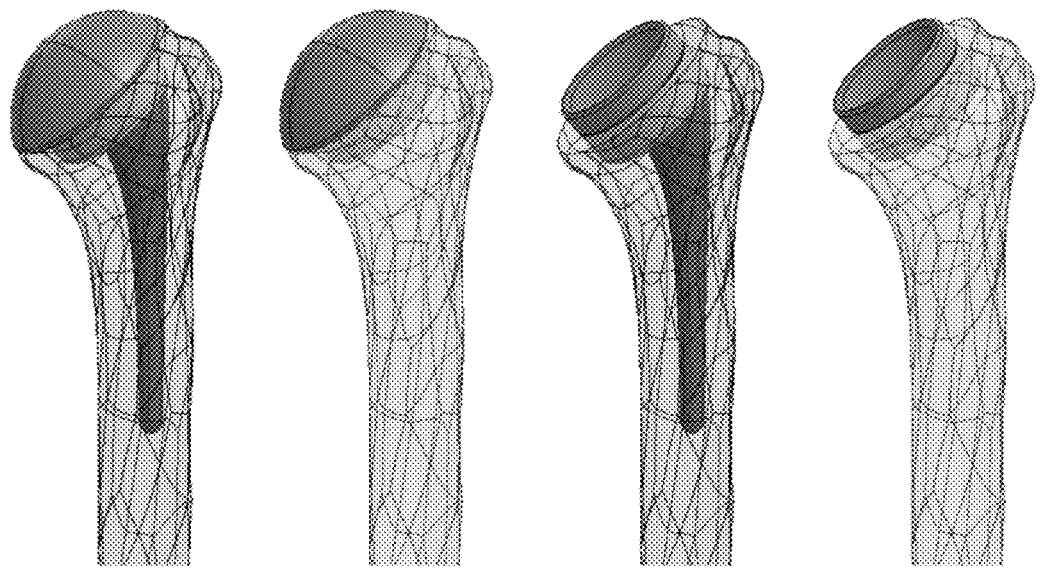
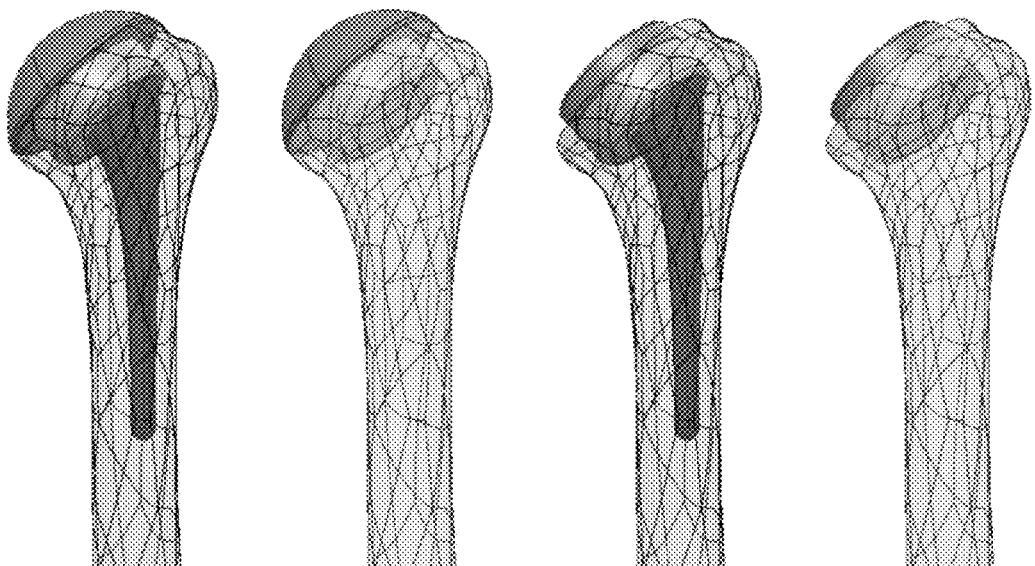

FIG 9
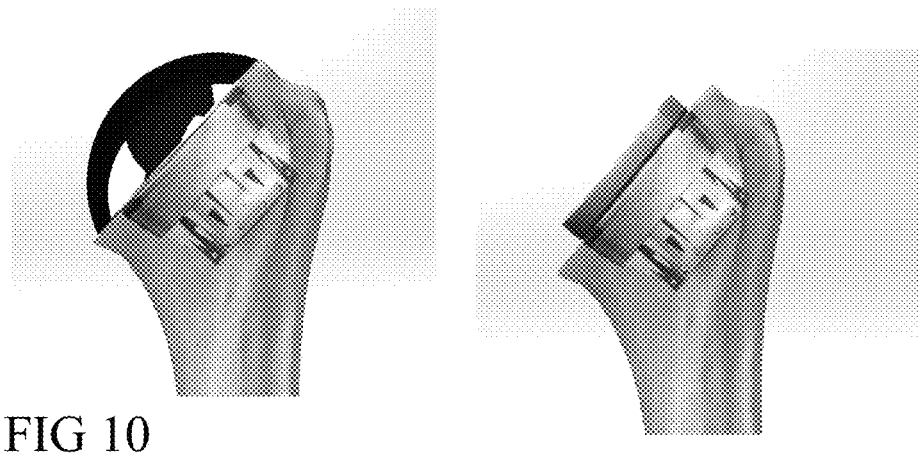
FIG 10
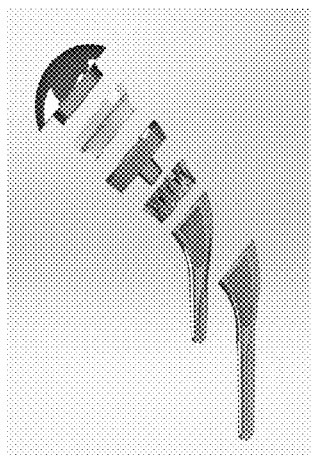
FIG 11
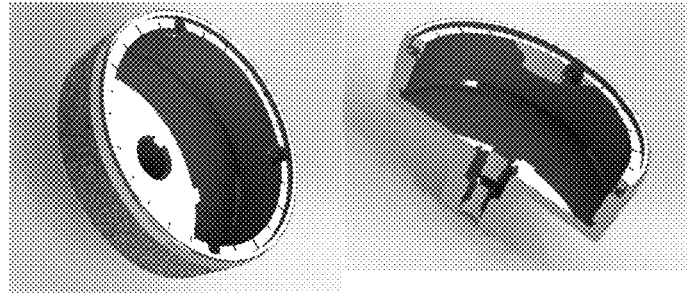
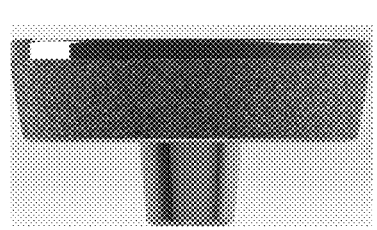
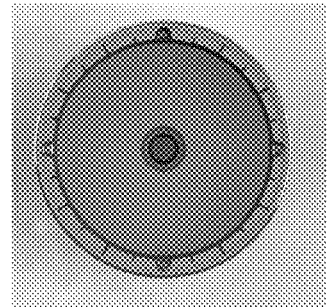

FIG 16

| Table I Prosthetic humeral head set measurements | | | | | | | | | | |
|---|---|---|---|---|---|---|---|---|---|---|
| A Sets | | | | | | | | | | |
| Head count/set | Spherical set measurements (mm) | | | | | Elliptical set measurements (mm) | | | | |
| | Df | HHH | ROCf | Ds | ROCs | Df | HHH | ROCf | Ds | ROCs |
| 1 | 40 | 15.2 | 20.7 | 40 | 20.7 | 40 | 15.2 | 20.7 | 38.4 | 19.8 |
| 2 | 44 | 16.4 | 22.8 | 44 | 22.8 | 44 | 16.4 | 22.8 | 41.2 | 21.6 |
| 3 | 48 | 17.6 | 24.9 | 48 | 24.9 | 48 | 17.6 | 24.9 | 43.9 | 23.3 |
| 4 | 52 | 18.8 | 27.1 | 52 | 27.1 | 52 | 18.8 | 27.1 | 46.7 | 25.1 |
| 5 | 56 | 20 | 29.2 | 56 | 29.2 | 56 | 20.0 | 29.2 | 49.4 | 26.8 |
| B Sets | | | | | | | | | | |
| Head count/set | Spherical set measurements (mm) | | | | | Elliptical set measurements (mm) | | | | |
| | Df | HHH | ROCf | Ds | ROCs | Df | HHH | ROCf | Ds | ROCs |
| 1 | 40 | 15.2 | 20.7 | 40 | 20.7 | 40 | 15.2 | 20.7 | 38.4 | 19.8 |
| 2 | 43 | 16.1 | 22.3 | 43 | 22.3 | 43 | 16.1 | 22.3 | 40.5 | 21.1 |
| 3 | 46 | 17 | 23.9 | 46 | 23.9 | 46 | 17.0 | 23.9 | 42.5 | 22.4 |
| 4 | 49 | 17.9 | 25.5 | 49 | 25.5 | 49 | 17.9 | 25.5 | 44.6 | 23.8 |
| 5 | 52 | 18.8 | 27.1 | 52 | 27.1 | 52 | 18.8 | 27.1 | 46.7 | 25.1 |
| 6 | 55 | 19.7 | 28.7 | 55 | 28.7 | 55 | 19.7 | 28.7 | 48.8 | 26.4 |
| C Sets | | | | | | | | | | |
| Head count/set | Spherical set measurements (mm) | | | | | Elliptical set measurements (mm) | | | | |
| | Df | HHH | ROCf | Ds | ROCs | Df | HHH | ROCf | Ds | ROCs |
| 1 | 40 | 15.2 | 20.7 | 40 | 20.7 | 40 | 15.2 | 20.7 | 38.4 | 19.8 |
| 2 | 42 | 15.8 | 21.8 | 42 | 21.8 | 42 | 15.8 | 21.8 | 39.8 | 20.7 |
| 3 | 44 | 16.4 | 22.8 | 44 | 22.8 | 44 | 16.4 | 22.8 | 41.2 | 21.6 |
| 4 | 46 | 17 | 23.9 | 46 | 23.9 | 46 | 17.0 | 23.9 | 42.5 | 22.4 |

FIG 16 (cont)

| Head count/set | Df | HHH | ROCf | Ds | ROCs | Df | HHH | ROCf | Ds | ROCs |
|---|---|---|---|---|---|---|---|---|---|---|
| 5 | 48 | 17.6 | 24.9 | 48 | 24.9 | 48 | 17.6 | 24.9 | 43.9 | 23.3 |
| 6 | 50 | 18.2 | 26.0 | 50 | 26.0 | 50 | 18.2 | 26.0 | 45.3 | 24.2 |
| 7 | 52 | 18.8 | 27.1 | 52 | 27.1 | 52 | 18.8 | 27.1 | 46.7 | 25.1 |
| 8 | 54 | 19.4 | 28.1 | 54 | 28.1 | 54 | 19.4 | 28.1 | 48.1 | 26.0 |
| 9 | 56 | 20 | 29.2 | 56 | 29.2 | 56 | 20.0 | 29.2 | 49.4 | 26.8 |

D Sets

| Head count/set | Spherical set measurements (mm) | | | | | Elliptical set measurements (mm) | | | | |
|---|---|---|---|---|---|---|---|---|---|---|
|  | Df | HHH | ROCf | Ds | ROCs | Df | HHH | ROCf | Ds | ROCs |
| 1 | 40 | 15.2 | 20.7 | 40 | 20.7 | 40 | 15.2 | 20.7 | 38.4 | 19.8 |
| 2 | 41 | 15.5 | 21.2 | 41 | 21.2 | 41 | 15.5 | 21.2 | 39.1 | 20.2 |
| 3 | 42 | 15.8 | 21.8 | 42 | 21.8 | 42 | 15.8 | 21.8 | 39.8 | 20.7 |
| 4 | 43 | 16.1 | 22.3 | 43 | 22.3 | 43 | 16.1 | 22.3 | 40.5 | 21.1 |
| 5 | 44 | 16.4 | 22.8 | 44 | 22.8 | 44 | 16.4 | 22.8 | 41.2 | 21.6 |
| 6 | 45 | 16.7 | 23.4 | 45 | 23.4 | 45 | 16.7 | 23.4 | 41.9 | 22.0 |
| 7 | 46 | 17 | 23.9 | 46 | 23.9 | 46 | 17.0 | 23.9 | 42.5 | 22.4 |
| 8 | 47 | 17.3 | 24.4 | 47 | 24.4 | 47 | 17.3 | 24.4 | 43.2 | 22.9 |
| 9 | 48 | 17.6 | 24.9 | 48 | 24.9 | 48 | 17.6 | 24.9 | 43.9 | 23.3 |
| 10 | 49 | 17.9 | 25.5 | 49 | 25.5 | 49 | 17.9 | 25.5 | 44.6 | 23.8 |
| 11 | 50 | 18.2 | 26.0 | 50 | 26.0 | 50 | 18.2 | 26.0 | 45.3 | 24.2 |
| 12 | 51 | 18.5 | 26.5 | 51 | 26.5 | 51 | 18.5 | 26.5 | 46.0 | 24.6 |
| 13 | 52 | 18.8 | 27.1 | 52 | 27.1 | 52 | 18.8 | 27.1 | 46.7 | 25.1 |
| 14 | 53 | 19.1 | 27.6 | 53 | 27.6 | 53 | 19.1 | 27.6 | 47.4 | 25.5 |
| 15 | 54 | 19.4 | 28.1 | 54 | 28.1 | 54 | 19.4 | 28.1 | 48.1 | 26.0 |
| 16 | 55 | 19.7 | 28.7 | 55 | 28.7 | 55 | 19.7 | 28.7 | 48.8 | 26.4 |
| 17 | 56 | 20 | 29.2 | 56 | 29.2 | 56 | 20.0 | 29.2 | 49.4 | 26.8 |

FIG 17

Table II Results based on head type and number of heads per set

| Comparison Group | Head type | Number of heads/set | % of population replicated within 3mm | | Head type | Number of heads/set | % of population replicated within 3mm | Adequately powered? (post hoc) | Power (1-beta) (post hoc) | Sample size (N1-N2) needed for adequate power (a priori) | Difference statistically significant with Fisher exact test | P value |
|---|---|---|---|---|---|---|---|---|---|---|---|---|
| 1 | spherical | 5 | 41% | vs | elliptical | 5 | 96% | Yes | 1.000 | n/a | Yes | 0.0001 |
|   |   | 6 | 66% |   |   | 6 | 99% | Yes | 1.000 | n/a | Yes | 0.0001 |
|   |   | 9 | 71% |   |   | 9 | 99% | Yes | 1.000 | n/a | Yes | 0.0001 |
|   |   | 17 | 78% |   |   | 17 | 100% | Yes | 0.999 | n/a | Yes | 0.0001 |
| 2 | spherical | 5 | 41% | vs | elliptical | 5 | 96% | Yes | 1.000 | n/a | Yes | 0.0001 |
|   |   | 6 | 66% |   |   | 6 | 96% | Yes | 1.000 | n/a | Yes | 0.0001 |
|   |   | 9 | 71% |   |   | 9 | 96% | Yes | 0.997 | n/a | Yes | 0.0001 |
|   |   | 17 | 78% |   |   | 5 | 96% | Yes | 0.955 | n/a | Yes | 0.0013 |
| 3 | spherical | 5 | 41% | vs | spherical | 6 | 66% | Yes | 0.313 | 1393.1393 | Yes | 0.0023 |
|   |   | 5 | 41% |   |   | 9 | 71% | Yes | 0.273 | 234.234 | Yes | 0.0002 |
|   |   | 5 | 41% |   |   | 17 | 78% | Yes | 0.999 | n/a | Yes | 0.0001 |
|   |   | 6 | 66% |   |   | 17 | 78% | No | 0.131 | 635.635 | No | 0.0531 |
|   |   | 6 | 66% |   |   | 17 | 78% | No | 0.449 | * | No | 0.1596 |
|   |   | 9 | 71% |   |   | 17 | 78% | No | 0.111 | * | No | 0.3604 |
| 4 | elliptical | 5 | 96% | vs | elliptical | 6 | 99% | No | 0.061 | 444,444 | No | 0.6202 |
|   |   | 5 | 96% |   |   | 9 | 99% | No | 0.061 | 444,444 | No | 0.6202 |
|   |   | 5 | 96% |   |   | 17 | 100% | No | 0.189 | 197,197 | No | 0.2432 |
|   |   | 6 | 99% |   |   | 9 | 99% | No | 0.050 | * | No | 1.0000 |
|   |   | 6 | 99% |   |   | 17 | 100% | No | 0.061 | 790,790 | No | 1.0000 |
|   |   | 9 | 99% |   |   | 17 | 100% | No | 0.061 | 790,790 | No | 1.0000 | n/a - not applicable; * - sample size cannot be calculated a priori when there is no difference between groups

FIG 18

Table III Results analyzed by dimensional parameter

| | | | # of specimens where anatomy could not be replicated within 3mm, listed by parameter (n = 79) | | | | # of specimens where 1 or more parameter was not replicated (n = 79) |
|---|---|---|---|---|---|---|---|
| Set | Head type | # heads/set | Ds | ROCf | ROCs | HHH | |
| A | spherical | 5 | 46 | 1 | 5 | 0 | 47 |
| B | spherical | 6 | 27 | 0 | 2 | 0 | 27 |
| C | spherical | 9 | 23 | 0 | 2 | 0 | 23 |
| D | spherical | 17 | 17 | 0 | 1 | 0 | 17 |
| A | elliptical | 5 | 2 | 1 | 1 | 0 | 3 |
| B | elliptical | 6 | 1 | 0 | 0 | 0 | 1 |
| C | elliptical | 9 | 1 | 0 | 0 | 0 | 1 |
| D | elliptical | 17 | 0 | 0 | 0 | 0 | 0 |

Ds - diameter of the base of the humeral head in the sagittal plane; ROCf - radius of curvature in the frontal plane; ROCs - radius of curvature of the humeral head in the sagittal plane; HHH - humeral head height FIG 20
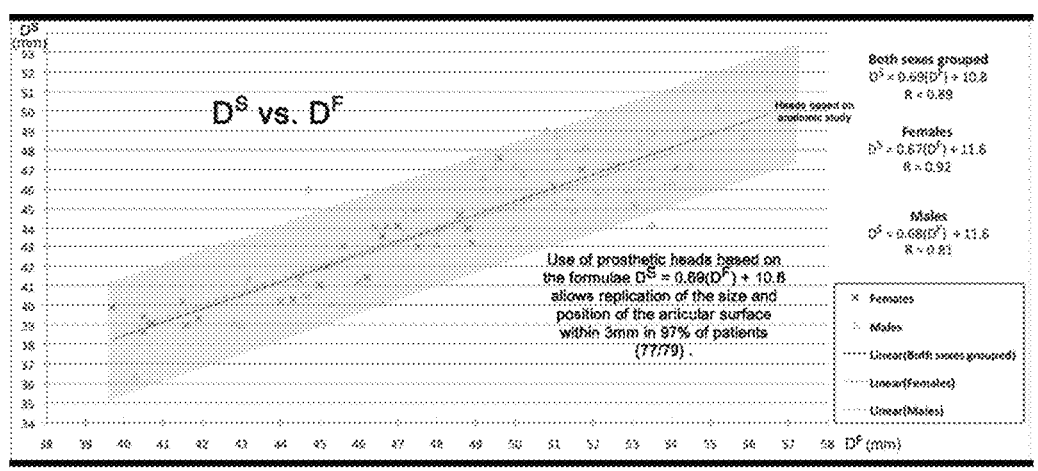
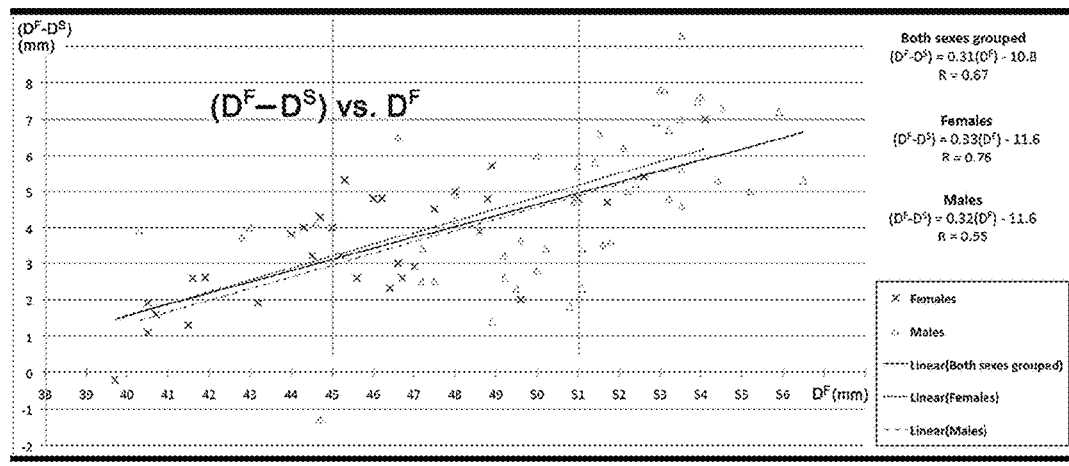

FIG 21
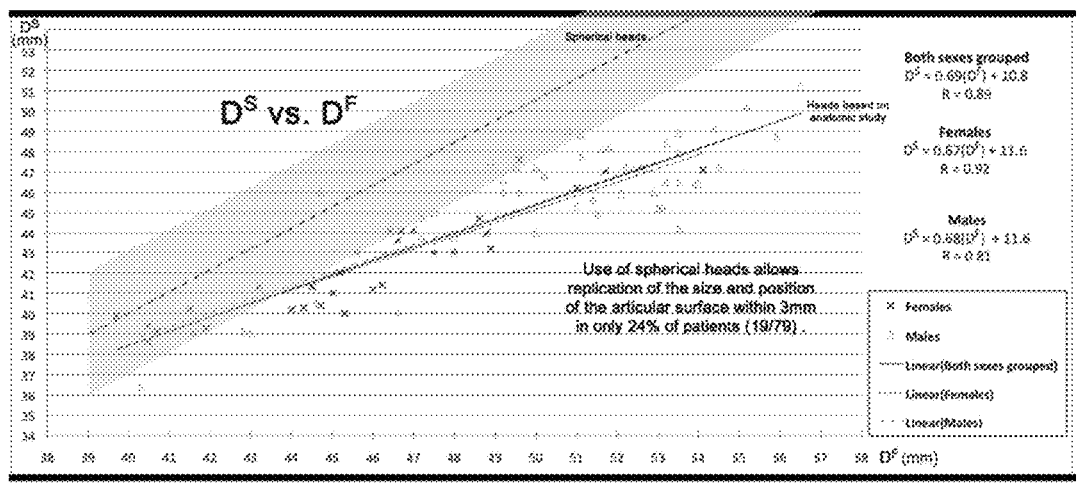
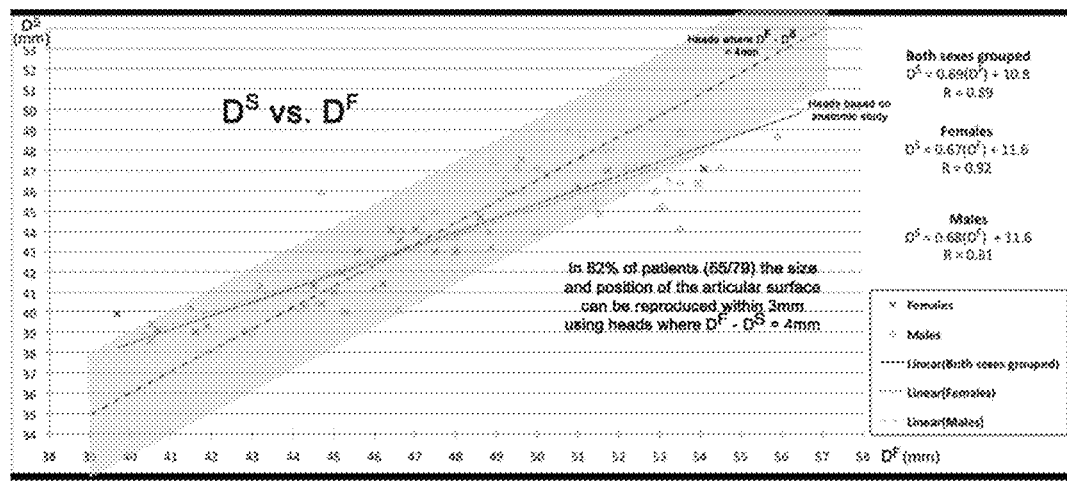

ARTHROPLASTY IMPLANTS AND METHODS FOR ORIENTING JOINT PROSTHESIS

RELATED APPLICATIONS

This application is continuation in part of U.S. patent application Ser. No. 14/586,677 filed on Dec. 30, 2014, and also claims the benefit of the filing dates of U.S. Provisional Patent Application Nos. 61/921,593 filed Dec. 30, 2013, and 61/928,399 filed Jan. 16, 2014, and U.S. Provisional Patent Application No. 62/490,395 filed Apr. 26, 2017, and U.S. patent application Ser. No. 15/263,012 filed on Sep. 12, 2016, now granted, and U.S. Provisional Patent Application Nos. 62/217,695 filed on Sep. 11, 2015, and 62/217,703 filed on Sep. 11, 2015, the contents of which are incorporated by reference herein, in their entirety. This application is related to PCT Application No. PCT/US14/72845 filed Dec. 30, 2014.

FIELD

The disclosure relates to the field of joint replacement, and more particularly total shoulder arthroplasty using prosthetic components.

BACKGROUND

Anatomic and Non-Anatomic Shoulder Replacement

In the field of shoulder arthroplasty, there are two general and somewhat competing points of view regarding the state of the patient's anatomy. From the point of view of some clinicians, it is desirable to aim for restoration of the native anatomy through use of prosthetic shoulder components that are shaped in a manner that is anatomically correct, particularly with regards to the shape of the prosthetic humeral head. For others, the higher objective is to aim for adapting and balancing the existing soft tissues, particularly the rotator cuff and musculature, with the shape and orientation of the replacement humeral head, even if the shape of the prosthetic head is not anatomically correct.

The anatomic approach involves restoration of the humeral head to its pre-diseased state, with utilization of spherical humeral head components with proportional diameter and thickness. In contrast, the non-anatomic approach involves humeral head replacement with soft-tissue balancing of the rotator cuff utilizing spherical humeral head components of varying thicknesses. Generally, within the art, reverse shoulder arthroplasty is considered non-anatomic shoulder replacement because the native glenoid side of the shoulder is converted to a sphere to mimic the humerus (glenosphere), while the humeral side is converted to mimic a glenoid (typically through replacement of the humeral head with a cup shaped implant).

Desired features of anatomic implants include replication of humeral neck angle, version, and posterior and medial offset. In the current art, stemmed arthroplasty systems are the most prevalent, and essentially all stemmed arthroplasty systems use spherical humeral heads. The conventional belief is that roughly one-third of a sphere is considered to be the most anatomically correct shape of the current offerings. Regardless of head size, the ratio of the head height to the radius of curvature is about 3:4. Clinical outcomes in patients who have received anatomically correct prostheses are generally regarded as superior when compared to soft-tissue balancing techniques using non-anatomically shaped (i.e., anatomically incorrect) prostheses.

A challenge in the art is the absence of anatomically correct head articulation surfaces. It is known that the native anatomical shape of the humeral head is not spherical, but elliptical (i.e., where the cross section of the humeral head has a radius of curvature in the superior to inferior dimension that is greater than the radius of curvature of the cross section in the anterior to posterior dimension). Recent research has shown that a prosthetic humeral head having a cross sectional shape adjacent to the bone cut that is elliptically-shaped and a generally spherical center point would theoretically allow a patient to have improved shoulder range of motion and function postoperatively. However, because the center of rotation of the humeral head is offset from the long axis of the humeral bone, it has been impractical for any shoulder implant company to create a prosthesis with an elliptically-shaped prosthetic humeral head. Merely coupling an elliptically-shaped head with a traditional stemmed prosthesis design would present difficulties accounting for the surgeon's need to simultaneously achieve the proper head size, correct rotational orientation of the elliptical head, and the proper amount of superior to inferior and anterior to posterior offset relative to the stem. Moreover, in many shoulder surgeries, only the humeral portion of the joint is replaced while the native glenoid is left intact, presenting a challenge of matching the articulating surface of the head prosthetic with the native articulating surface of the glenoid. This challenge is not present in total arthroplasty, where both the humeral and the glenoid portions are replaced with prosthetics.

Ideally, a shoulder arthroplasty system would provide a wide range of head choices and offsets to most precisely match the patient's native anatomy. With such a system, a near perfect match could be achieved in a hemi-arthroplasty, and if the system were modular, could be adapted in a revision to provide an ideal match if the shoulder is converted to either a total arthroplasty or to a reverse shoulder arthroplasty. The current art does not provide such modular systems, thus, to accomplish the desirable offsets with traditional stem designs, whether using spherical or elliptical heads, it would be necessary to stock an essentially infinite inventory of prosthetic heads and/or stems with variable offsets for achieving the desired shape, size and positioning, which is, of course, economically impractical.

SUMMARY

In the various embodiments, elliptical humeral head implants are provided, and systems, assemblies, and methods comprising the same.

In some embodiments a system for long bone arthroplasty is provided that includes prosthesis components characterized as having a convex articulation surface that is hemielliptical and is defined by a major axis (corresponding to a frontal plane) and a minor axis (corresponding to a sagittal plane), a major diameter (DF) along the major axis and a minor diameter (DS) along the minor axis, and radii of curvature along the major axis (ROCF) and along the minor axis (ROCS), each prosthesis component comprising an apex and a base each having an elliptical cross sectional shape. In a representative embodiment, the system includes an array of humeral head prosthesis components, each humeral head prosthesis component in the array having a convex articulation surface that is hemielliptical and is defined by a major axis (corresponding to a frontal plane)

and a minor axis (corresponding to a sagittal plane), a major diameter (DF) along the major axis and a minor diameter (DS) along the minor axis, and radii of curvature along the major axis (ROCF) and along the minor axis (ROCS), each prosthesis component comprising an apex and a base each having an elliptical cross sectional shape.

In some such embodiments, the array includes a plurality of prosthesis components that (i) vary from one another in their major diameters in a range from about 1 to 4 mm, and (ii) vary from one another in at least one of minor diameter, humeral head height (HHH), ROCF and ROCS as a function of DF. In accordance with some embodiments, the plurality of humeral head prosthesis components that vary from one another are characterized as varying from having a base with a more circular cross-sectional shape to a more elongated elliptical cross-sectional shape with increasing DF. In accordance with some embodiments, DF varies across the plurality of humeral head prostheses in the range from about 40 mm to about 56 mm. In accordance with some embodiments, DF varies across the plurality of humeral head prostheses in the range from at least 40 mm to no more than 56 mm. In accordance with some embodiments, the array of elliptical humeral head prosthesis components provides for anatomical fit relative to a native humeral head within a variation of up to and not more than 3 mm in one or both of the DF and DS dimensions in at least 96% and up to 99% of a patient population in which a native humeral head has a minor diameter that is equal to 0.69 times a major diameter plus an additional length in millimeters of 10.8 millimeters plus or minus 1 or 2 millimeters.

In accordance with some embodiments, the plurality of humeral head prosthesis components is selected from the group of (i) an array of 5 heads that vary from one another in the major diameter in 4 mm increments, (ii) an array of 6 heads that vary from one another in the major diameter in 3 mm increments, (iii) an array of 9 heads that vary from one another in the major diameter in 2 mm increments, and (iv) an array of an array of 17 heads that vary from one another in the major diameter in 1 mm increments.

In accordance with some embodiments, the system also includes at least one generally disc shaped coupler component having a central axis, and a prosthesis component side that includes a recess configured to interface with and engage the humeral head prosthesis component. The recess has in some embodiments a substantially planar floor and a sidewall and at least one prosthesis component engagement feature. The coupler also includes an opposing side having a bone contact surface, and a lateral edge that bounds the prosthesis component and opposing sides.

In accordance with various embodiments, an anatomical fit of a humeral head prosthesis component selected from the array is achieved by selecting a head based on size and by rotationally varying orientation of the selected head as compared with a native humeral head to most closely match a native anatomy of the native humeral head.

In accordance with various embodiments, upon implanting into a long bone, an orientation of the major and minor axes of the humeral head prosthesis component relative to a center axis of the long bone is determined at the coupler-prosthesis interface.

In accordance with some embodiments, the prosthesis component side of the coupler component is configured to interchangeably interface with and engage both a convex humeral head prosthesis component and a concave prosthesis component. According to such embodiments, the system further includes a non-elliptical prosthesis component selected from one or more of (i) at least one concave cup having a cross sectional shape that is circular, and (ii) a convex head having a cross sectional shape that is circular.

In accordance with some embodiments, the coupler component includes on the opposing side one or more of (i) a male taper, (ii) an anchor that is unitary with the coupler component and selected from a cage and a stem, and (iii) an anchor engagement feature extending from a surface and radially offset from the central axis. According to some such embodiments, the coupler component includes on its opposing side at least one anchor engagement feature extending from a surface and radially offset from the central axis. Further according to some such embodiments, the system also includes an anchor component that includes a proximal portion having a proximal surface for contacting at least a portion of the opposing side of the coupler component and a distal portion for positioning within a bone, the proximal portion of the anchor including on its proximal surface a coupler component engagement feature.

In another embodiment, an arthroplasty assembly includes a prosthesis component and a coupler component engageable to provide an arthroplasty assembly, wherein the position of the prosthesis component can be varied rotationally around a shared central engagement axis with the coupler component. According to such embodiments, the prosthesis component is selected from an array that includes a plurality of humeral head prosthesis components that (i) vary from one another in their major diameters in a range from about 1 to 4 mm, and (ii) vary from one another in at least one of minor diameter, humeral head height (HHH), ROCF and ROCS as a function of DF. Each humeral head prosthesis component in the array has a convex articulation surface that is hemielliptical and is defined by a major axis (corresponding to a frontal plane) and a minor axis (corresponding to a sagittal plane), a major diameter (DF) along the major axis and a minor diameter (DS) along the minor axis, and radii of curvature along the major axis (ROCF) and along the minor axis (ROCS). And each prosthesis component has an apex and a base each having an elliptical cross sectional shape. According to such embodiments, the coupler component includes a prosthesis component engagement side and an opposite side having a bone contact surface, and the sides are bounded by a lateral edge that is one of cylindrical, frustoconical and frustohemispherical. According to such embodiments, when one of the selected prosthesis and coupler components are engaged and the coupler component is recessed into bone, rotation of the prosthesis component within the coupler component provides alignment of the bone articulation surface of the prosthesis component with the bone that is anatomically similar to a native long bone.

In accordance with some embodiments, the assembly is anchorless. In other embodiments, the assembly includes an anchor component, and the coupler component is selected from an array that includes of a plurality of coupler components, each of which includes on its opposing side a variably positioned anchor engagement feature. According to such embodiments, each of at least two of the plurality of coupler components has at least one anchor engagement feature that is off-center from a center point of the coupler component, the off-center engagement feature on each of the at least two coupler components at a different distance in at least one dimension relative to the center point. In some such embodiments, the anchor component is selected from an array that includes a plurality of anchor components each having a proximal portion with a proximal surface for contacting at least a portion of the coupler component and a distal portion for positioning within bone. According to some such embodiments, the proximal portion has an angle of inclination relative to the long bone into which it is to be implanted of from about 120 to about 145 degrees, and also includes a coupler component engagement feature.

In yet another embodiment, a method for implanting a modular system for long bone arthroplasty the method includes use of an arthroplasty assembly according to one of the foregoing embodiments. The method further includes selecting coupler and prosthesis components, at least provisionally fitting the selected coupler component into a metaphysis of a long bone; and engaging the selected prosthesis component into the recess of the prosthesis component side of the coupler component. In some embodiments, the assembly is anchorless. In other embodiments, the coupler component includes on the opposing side, one or more of a male taper, an anchor that is unitary with the coupler component and selected from a cage and a stem, and an anchor engagement feature extending from a surface and radially offset from the central axis. According to some specific embodiments, the method includes use of a coupler component that has at least one anchor engagement feature extending from the bone contact surface and radially offset from the central axis, and an anchor component that has a proximal portion with a proximal surface for contacting at least a portion of the anchor component side of the coupler component and a distal portion for positioning within a bone. According to some such embodiments, the proximal portion includes on its proximal surface a coupler component engagement feature, wherein an orientation of the major and minor axes of the humeral head prosthesis component relative to a center axis of the long bone is determined at the coupler-prosthesis interface, and wherein an offset of the prosthesis component from the center axis of the long bone is determined at the anchor-coupler interface.

BRIEF DESCRIPTION OF THE DRAWINGS

Features and advantages of the general inventive concepts will become apparent from the following description made with reference to the accompanying drawings, including drawings represented herein in the attached set of figures, of which the following is a brief description:

FIG. 2 shows a hemi view of a humeral head prosthesis and alternate frontal and side views of a bone cut line on a humerus, indicating the diameter and radius of curvature of each of the frontal and sagittal planes;

FIG. 8 shows front and back perspective views of anchored and anchorless embodiments of a modular arthroplasty assembly including a spherical head articulation surface (left two images, top and bottom) and a concave cup articulation surface (right two images, top and bottom) assembled in the context of a humerus;

FIG. 9 shows side views of stemless embodiments (with a cage) of a modular arthroplasty assembly including a spherical head articulation surface (left image) and a concave cup articulation surface (right image) assembled in the context of a humerus;

FIG. 10 shows an exploded side view of an embodiment of a modular arthroplasty assembly with a stem, showing alternate stem lengths and alternate embodiments of an articulation surface ("prosthetic component") in the form of a spherical head and a concave poly cup;

FIG. 11 shows from top left to bottom right, alternate top perspective and cross-sectional top perspective, side and top views of an embodiment of a coupler/metaphyseal shell;

FIG. 16 shows a table designated TABLE I that provides parameter measurements for prosthetic humeral head sets A-D;

FIG. 17 shows a table designated TABLE II that provides results based on head type and number of heads per set;

FIG. 18 shows a table designated TABLE III that provides results with arrays of heads analyzed by dimensional parameter;

FIG. 20 shows scatter plots with linear trend lines demonstrating in the upper panel graphic the formulae from the anatomical stud and in the lower panel graphic the mathematical relationship between the length difference between the head axes in the frontal and sagittal planes (DF-DS) and the diameter of the base of the head in the frontal plane (DF);

FIG. 21 shows scatter plots with linear trend lines demonstrating in the upper panel graphic the formulae from the anatomical study versus spherical heads, and in the lower panel graphic the formulae from the anatomical study versus heads with a fixed 4 mm difference (DF-DS);

DESCRIPTION

Figure 1:
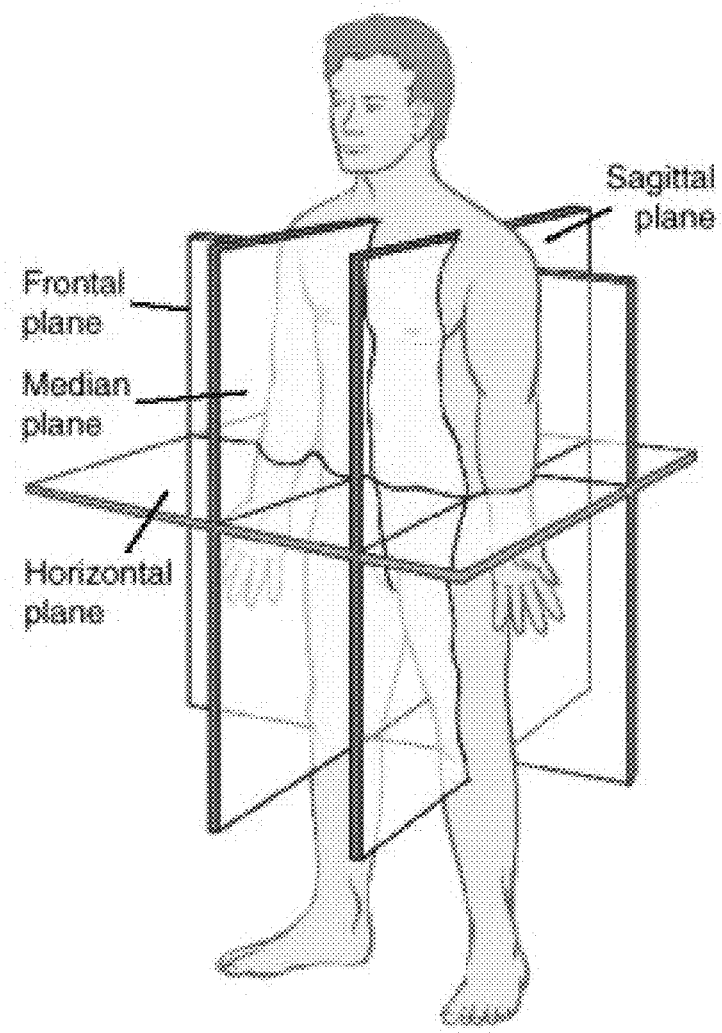
FIG. 1 is a diagram showing the transverse, frontal and sagittal planes in the context of human anatomy.

This disclosure describes exemplary embodiments in accordance with the general inventive concepts and is not intended to limit the scope of the invention in any way. Indeed, the invention as described in the specification is broader than and unlimited by the exemplary embodiments and examples set forth herein, and the terms used herein have their full ordinary meaning.

The general inventive concepts are described with occasional reference to the exemplary embodiments and the exemplary embodiments depicted in the drawings. Unless otherwise defined, all technical and scientific terms used herein have the same meaning as commonly understood by one of ordinary skill in the art encompassing the general inventive concepts. The terminology set forth in this detailed description is for describing particular embodiments only and is not intended to be limiting of the general inventive concepts.

Arrays of Elliptical Heads

Recent studies suggest that rotational range of motion and glenohumeral joint kinematics might be improved during shoulder arthroplasty by employing a prosthetic humeral head that is elliptical in shape rather than spherical. While previous anatomical studies have documented that the shape of the humeral head is elliptical or ovoid, no study to date has examined whether or not the elliptical shape changes dimensionally with increasing humeral head size. Based on the inventors' unexpected findings about the dimensional relationships of the heads of humerii as the heads increase in size, provided herein in various embodiments are systems and implants for long bone arthroplasty.

Provided are novel elliptical humeral head prostheses and arrays of elliptical humeral head prostheses, systems, and methods including the same.

Figure 7:
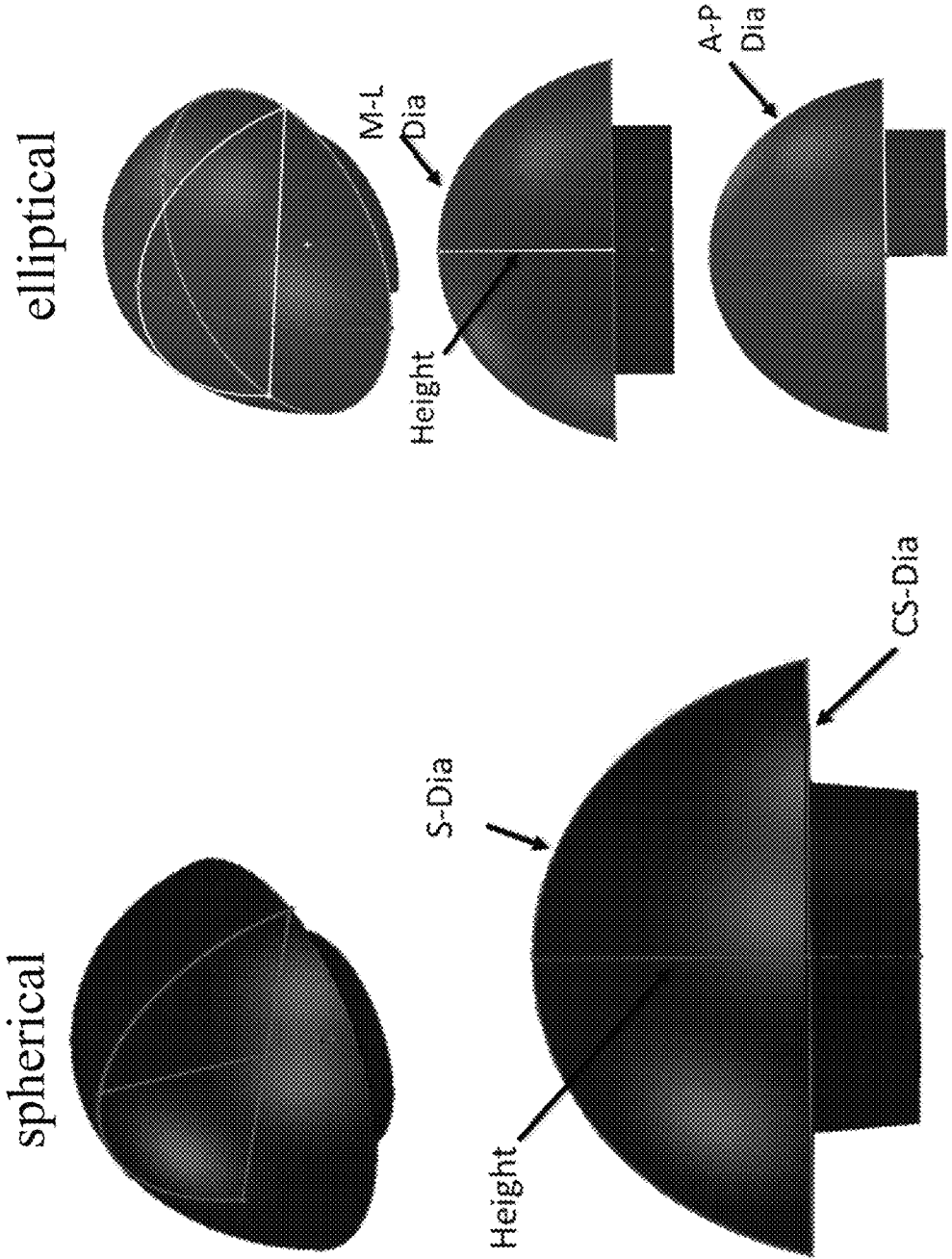
FIG. 7 shows side and perspective views of a spherical humeral head prosthesis and a elliptical humeral head prosthesis indicating the frontal and sagittal diameters and radii of curvature.

Referring now to the drawings, as shown in FIG. 1 and FIG. 7, and as described herein in the context of the native anatomy, the major diameter is the diameter at the base of the humeral head in the frontal plane (DF-from S to I) and the minor diameter is the diameter in the sagittal plane (DS-from A to P). Each humeral head prosthesis component in the array has a major diameter and a minor diameter that are not equal, and each of these features is also different from each of the other humeral head prosthesis components in the array. Comparing at two or more prostheses in the array, as the major diameter increases, the ratio of the minor diameter to the major diameter decreases, whereby from smaller to larger, the humeral head prosthesis components vary from having a base with a more circular cross sectional shape to a more elongated elliptical cross sectional shape with increasing size.

Much emphasis has been placed on replicating normal, prepathologic anatomy during shoulder reconstructive surgery. Use of a prosthetic humeral head that is inaccurately sized or positioned may lead to poor clinical outcomes, including shoulder stiffness and rotator cuff tearing. It has been reported that alterations to humeral head geometry may produce eccentric loading at a prosthetic glenoid that may contribute to early component wear and loosening. And biomechanical studies have confirmed that altering the size and position of the articular surface by as little as 4 or 5 mm changes the kinematics and forces across the glenohumeral joint. Thus, a goal in shoulder arthroplasty is to replicate as closely as possible the size and position of the articular surface at the base of the humeral head so that it is within 3 mm of the normal anatomy.

The inventors have made the surprising discovery that the native anatomy of humeral heads varies from what has been conventionally understood. Referring to the drawings, FIG. 7 depicts relationships of features of spherical and elliptical heads. The elliptical shape of the humeral head has been vaguely described and as mentioned herein above, and others have described the average difference between the DF and DS measurements at the humeral head base from about 2 mm, to about 3.9 on average. The inventors are the first to show that the elliptical shape of the base of the humeral head seems to elongate in the frontal plane as head size increases, and thus, the relationship between DF and DS is not a constant.

The inventors have recognized that compared to spherical prosthetic heads, use of elliptical heads resulted in improved replication of the normal humeral head shape. And regardless of the number of available head sizes per set, it was possible to replicate the normal anatomy within 3 mm in a higher percentage of specimens using elliptical (96-100%) as opposed to spherical (41-78%) prosthetic heads ($P \leq 0.0013$). In some embodiments, according to the instant disclosure, elliptical humeral head prostheses having an elliptical articulation surface are provided in arrays, including, a set comprising as few as five (5) elliptical heads can match about 96% of a patient population, and about six (6) elliptical heads can match about 99% of a patient population. One or more of the heads in an array is selected for combination with at least a coupler (convertible offset coupler/metaphyseal shell) and in some embodiments an anchor.

Based on the newly developed understanding of the relationship of the shape and size of native elliptical humeral heads in the frontal and sagittal planes, the inventors provide here in some embodiments is a novel system of humeral head prostheses having anatomically relevant shapes that overcome the shortcomings in the existing art with respect to anatomically relevant shape that can positively influence clinical outcomes for arthroplasty patients. These novel humeral heads have the feature of being hemi elliptical, with elliptical apexes and with elliptical bases (essentially at a base that would correspond with the bone cut made at the base of an anatomical head of a humerus).

Sets of Arrays

In one exemplary embodiment prosthesis components for long bone arthroplasty are provided, the prosthesis components including an array of elliptical heads comprising from 5 to 17 elliptical heads is provided, wherein each head in the array of heads varies from the others in the diameters at the base of the head in both the frontal (DF) and sagittal (DS) planes, the radii of curvature in both the frontal (ROCF) and sagittal (ROCS) planes, and humeral head height (HHH). In some examples, four possible arrays of heads are contemplated, wherein the prosthetic heads of each head type vary in size within the array from small to large in 4, 3, 2, or 1 mm increments, wherein the values for the smallest to the largest heads is expressed as DF≥40 mm, and DF≤56 mm, respectively. In the various embodiments, the number of heads per array can vary from 5, 6, 9 and 17, based on the dimensional value by which the head size is incrementally increased: starting at 40 mm, wherein a 4 mm incremental increase in head size based on an increase of DF provides a set with 5 heads (Set A), a 3 mm incremental increase in head size based on an increase of DF provides a set with 6 heads (Set B), a 2 mm increase in head size based on an increase of DF provides a set with 9 heads (Set C), and a 1 mm increase in head size based on an increase of DF provides a set with 17 heads (Set D).

The arrays are adapted to cover the range of humeral head sizes based on anthropometric data to provide for suitable and sufficient anatomical fit within a variation of up to and not more than 3 mm in at least 96% of a patient population, and up to 99% of a patient population. The anatomical fit is achieved by selecting a head from the array based on size and by varying the orientation of the selected head positioned in the bone to most closely match the native anatomy of a humeral head diameters of the base of the head in both the frontal (DF) and the sagittal (DS) planes, and the radii of curvature in both the frontal (ROCF) and sagittal (ROCS) plane.

In some particular embodiments, with reference to the formulae as set forth in FIG. 2, each of the other humeral head prosthesis components in the array is characterized by having a minor diameter (in millimeters) that is equal to 0.69 times the major diameter (in millimeters) plus an additional length in millimeters of 10.8 millimeters, plus or minus 3 millimeters. Thus, in some embodiments, each humeral head prosthesis component in the array is characterized by having a minor diameter (in millimeters) that is equal to 0.69 times the major diameter (in millimeters) plus an additional length in millimeters that ranges from 6.80 millimeters to 14.80 millimeters.

In yet other embodiments, with further reference to the formulae as shown in FIG. 2, each humeral head prosthesis component in the array may be characterized by the minor diameter having a length that is equal to (0.69 times the major diameter) plus 10.8 mm. And in other embodiments, each humeral head prosthesis component in the array may be characterized by the humeral head prosthesis having a height that is equal to (0.30 times the major diameter) plus 3.2 mm plus or minus 3 mm. In still other embodiments, each humeral head prosthesis component in the array may be characterized by the humeral head prosthesis having along the major axis a radius of curvature that is equal to (0.53 times the major diameter) minus 0.5 mm plus or minus 2 mm. And in still other embodiments, each humeral head prosthesis component in the array may be characterized by the humeral head prosthesis having along the minor axis a radius of curvature that is equal to (0.44 times the major diameter) plus 2.2 mm plus or minus 2 mm.

In further specific embodiments, each humeral head prosthesis component in the array may be characterized by the features of a minor diameter that ranges from about 36 to 51 mm, a major diameter that ranges from about 37 to about 56 mm. And in further specific embodiments, each humeral head prosthesis component in the array may be characterized by a ratio of the minor diameter to the major diameter ranges from 0.87 to 1. And in still other embodiments, each prosthesis component in the array may be characterized by an angle of inclination ranges from 120 degrees to 143 degrees. And in still other embodiments, each prosthesis component in the array may be characterized by and a height of the humeral head prosthesis ranges from about 12 to 25 mm.

It will be appreciated in view of the data provided herein, together with the formulae developed by the inventors, that one or more than one of the above described features may characterize humeral head prosthesis components within the disclosure. And further still, that one or more unique arrays may be provided wherein the two or more prosthesis components in the array include one or any combination of the above described features, such arrays suited to one or more of specific patient populations that represent smaller or larger overall body types, or ethnic or geographical origins. Thus, it should be understood that the examples provided herein with respect to the reported data, and the representative examples of humeral head prostheses and arrays are not limiting and are merely representative of the possible arrays which can be provided based on the disclosure.

In accordance with some embodiments, a humeral head prosthesis is provided that is characterized by one or more of the features selected from the group including:

(i) a difference between the major and minor diameters (DMaj–DMin) and the ratio of the minor to major diameters (DMin/DMaj), wherein DMaj–DMin ranges from about 1 to about 15 mm, and wherein DMin/DMaj ranges from about 1 to about 0.8;

(ii) the minor diameter having a length that is equal to (0.69 times the major diameter) plus 10.8 mm, the humeral head prosthesis having a height that is equal to (0.30 times the major diameter) plus 3.2 mm plus or minus 3 mm, the humeral head prosthesis having along the major axis a radius of curvature that is equal to (0.53 times the major diameter) minus 0.5 mm plus or minus 2 mm, the humeral head prosthesis having along the minor axis a radius of curvature that is equal to (0.44 times the major diameter) plus 2.2 mm plus or minus 2 mm.

In some particular embodiments, the prosthesis component is characterized by the features of one of DMaj–DMin=2.6 and DMin/DMaj=0.94, DMaj–DMin=3.7 and DMin/DMaj=0.92, and DMaj–DMin=5.8 and DMin/DMaj=0.89. And in yet other embodiments, the humeral head prosthesis component is characterized by having a minor diameter (in millimeters) that is equal to 0.69 times the major diameter (in millimeters) plus an additional length in millimeters that ranges from 7.80 millimeters to 13.80 millimeters. And in still further embodiments, the humeral head prosthesis is characterized by one or more of the features selected from a minor diameter that ranges from about 36 to 51 mm, a major diameter that ranges from about 37 to about 56 mm, a ratio of the minor diameter to the major diameter ranges from 0.87 to 1, an angle of inclination ranges from 120 degrees to 143 degrees, and a height of the humeral head prosthesis ranges from about 12 to 25 mm.

It will be appreciated by one of ordinary skill that the various elliptical humeral head prostheses, and arrays of prostheses may be provided for use in conjunction with the modular systems and assemblies as described herein or may be adapted for use with other modular assemblies. And in some uses, the hemielliptical humeral heads as described herein may be adapted for use in monolithic designs that include an attached anchor rather than engageable with a modular anchor. Thus, it should be understood that the examples and representative embodiments are not limiting with respect to the use of the novel elliptical humeral head generally characterized by a ratio relationship of the minor diameter divided by the major diameter of the base, the array comprising a plurality of humeral head prosthesis components, each having a major diameter and a minor diameter that is different from each of the other humeral head prosthesis components in the array, wherein as the major diameter is increased the ratio of the minor diameter to the major diameter is decreased, whereby the humeral head prosthesis components vary from having a base with a more circular cross sectional shape to a more elongated elliptical cross sectional shape with increasing size.

According to the various embodiments, a modular system for long bone arthroplasty provides the elliptical headed prosthesis arrays, and one or more of coupler components (also referred to as metaphyseal shell) and optional anchor components that are engageable to provide an arthroplasty assembly wherein the position of the prosthesis component can be varied rotationally around a shared central engagement axis with the coupler component.

In some embodiments that comprise and anchor component, the position of the anchor component relative to the coupler component can be varied in two dimensions on a plane that is perpendicular to the central engagement axis of the coupler and prosthesis components by selecting the coupler component from an array comprising a plurality of coupler components that include variably positioned anchor engagement features. In accordance with such embodiments, each of at least two of the plurality of coupler components comprises at least one anchor engagement feature that is off-center from a center point of the coupler component, and the off-center engagement feature on each of the at least two coupler components is at a different distance in at least one dimension that is perpendicular to the central engagement axis.

In use, when the coupler, or the combination of coupler and anchor components are recessed into bone, the assembly achieves alignment of the bone articulation surface of the prosthesis component with the bone that is anatomically similar to a native long bone. In some embodiments the position of an elliptical head may be rotated at its engagement with the anchor to achieve the desired orientation relative to the bone.

In accordance with the various embodiments, the prosthesis component is adapted for engagement with one or the other of the coupler component or an anchor. In some embodiments, the head and the coupler are each adapted, respectively, with a male insert and a female receiver channel (such as a Morse type taper) for engagement there between. In accordance with the representative array of shells shown in FIG. 12 and FIG. 13, the dimensions of the engagement features, including the representative taper feature, may vary in length and diameter, and in general, the dimensions of these features can range from 5 mm to more than 100 mm. Thus, shells may be provided with engagement means, such as a taper, in heights and in greater and lesser diameters ranging in mm increments and fractions thereof from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to 100 mm.

Figure 12:
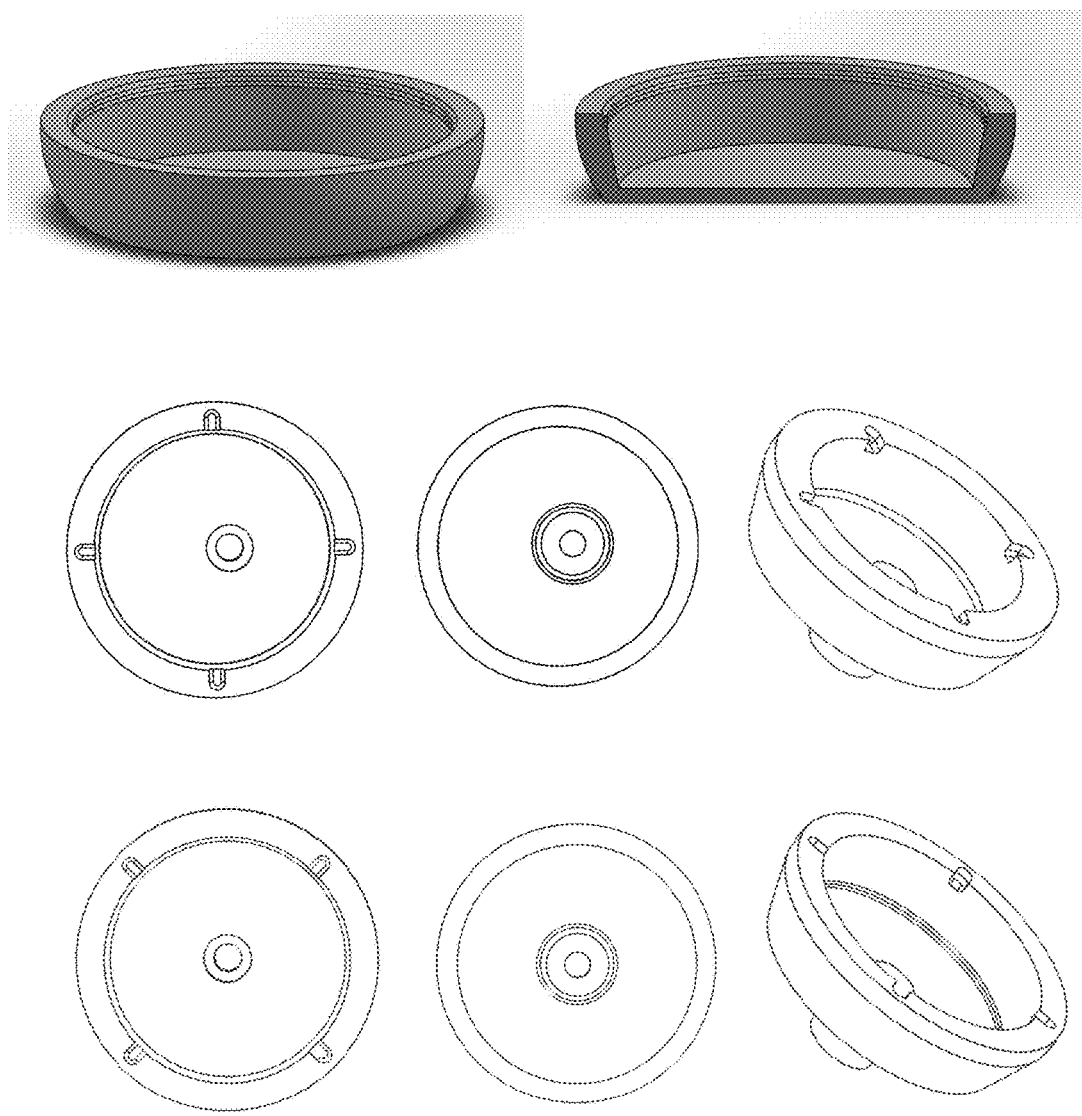
FIG. 12 shows in the top row alternate side and cross-sectional perspective views of an embodiment of a coupler/metaphyseal shell that lacks an anchor, and in each of the middle and bottom rows, top, bottom and top perspective views of a coupler/metaphyseal shell having one or two teeth and recess engagement features on the interior sidewall.
Figure 13:
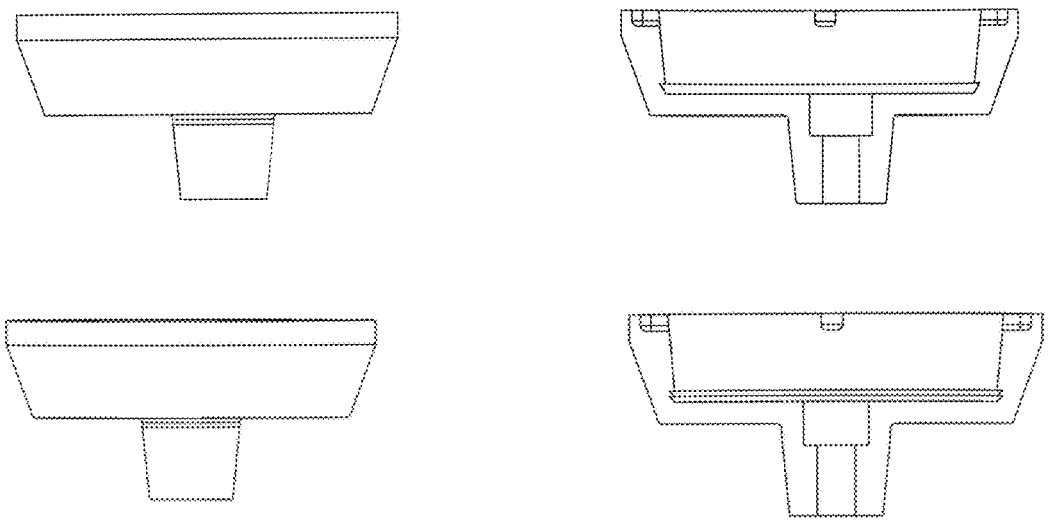
FIG. 13 shows in the top row a side view and a cross sectional side view of an embodiment of a coupler/metaphyseal shell having a frustohemispherical shape as shown in the center row of FIG. 12, and in the bottom row a side view and a cross sectional side view of an embodiment of a coupler/metaphyseal shell having a frustohemispherical shape as shown in the bottom row of FIG. 12.

Another engagement means provided on a shell is circumferential tabs or teeth that enable a snap fit, such as for engagement with a cup as shown in FIG. 39 and FIG. 44. Such features may be present in singular or as a plurality and may be positioned anywhere along the interior wall of the metaphyseal shell seat, including from the bottom to the top with any desired spacing there between and other optional interspersed surface features that may enhance fixation of a prosthesis component therein. Representative drawings that show detail of some embodiments of these engagement features are shown in FIG. 12 and FIG. 13, each of which drawings show side views of representative embodiments prosthesis components with engagement means in the form of concentric teeth positioned at the base of a taper on each of the alternate cup shaped implants. In some embodiments, the tabs or teeth may be notched to engage with corresponding splines or ribs to enable alignment and prevent axial displacement. Other means known in the art may be employed for engagement between the metaphyseal shell and prosthesis. In accordance with the representative array, the dimensions of the engagement features, including the representative tab features shown in the drawings, may vary in height and depth and spacing, and in general, the dimensions of these features can range from 0.1 mm to more than 20 mm. Thus, shells may be provided with the depicted engagement means, in mm increments and fractions thereof from 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, and 20 mm. Referring to the drawings, FIG. 12 and FIG. 13 each show alternate views of metaphyseal shells adapted with different engagement means which in the depicted embodiments are positioned at the base of the recess in the shells adjacent to the interior sidewalls thereof. It will be appreciated that the various engagement means are not intended to be limiting, and other engagement means that are not shown may be used, moreover, the engagement means may be used in the context of any form of prosthetic component and may be used interchangeably between them.

In some embodiments, the shells include on their prosthesis surfaces other features that aid in placement and in removal. For example, one or more slots or other access portals may be provided on a shell or plug component to enable passage of an osteotome or other device to facilitate freeing an implant from bone due to boney ingrowth thereupon. In addition, one or more circumferential tool engagement features such as are shown on the upper periphery of the interior wall of the metaphyseal shell embodiments shown in FIG. 11, FIG. 13 and FIG. 14, may be provided to aid in the placement and press-fit fixation of the shell into bone, and subsequent adjustment or removal thereof in the event of a revision surgery.

In some embodiments that further comprise prosthesis components selected from concave cups, the cup and the coupler are each adapted with an engagement means. In one embodiment, the engagement means comprises a snap fit tooth engagement feature. In some embodiments, the coupler includes engagement features that allow engagement and fixation with each of the head and cup prostheses. In other embodiments, a coupler is adapted with one or the other of head and cup prosthesis engagement features. Together, the components of the system, including the selectable engagement orientations of the components, enables adaptation to the existing anatomy of the patient and the ability to most closely achieve the native anatomy of the healthy shoulder joint so as to provide the patient with the most natural use of the shoulder.

Thus, as compared to other systems in the art, the disclosed system enables achievement of a more anatomically accurate joint replacement aimed at reducing clinically adverse consequences. And the coupler with its eccentric taper enables a wider range of selection of head/cup orientation without compromise of height, neck angle, version, and posterior and medial offset. This offset function, together with the anatomical benefits thereby attained, finally solves a vexing challenge in the art. That is, provision for truly adaptable and convertible, anatomically accurate implants-a challenge that has been heretofore addressed, inadequately at best, with either expansive prosthetic head inventory and/or adjustable systems that sacrifice one or more of the anatomically desirable implant features such as component height, neck angle, version, and posterior and medial offset.

This disclosure describes various exemplary convertible implant components and systems, convertible shoulder prosthesis systems, and methods for implantation of these. While the description below sets forth details of features of the modular arthroplasty assembly, one of skill will appreciate that the features may also be shared by other system components, such as those that are used to determine implant size and positioning, generally referred to as trials. Moreover, the features and elements as described herein for the shoulder and humerus may be readily adapted for use in the context of other long bones.

Humeral Head Prosthesis

Hemi Elliptical Heads

In accordance with the various embodiments, novel elliptical humeral head prostheses and systems for long bone arthroplasty are provided. The system comprises an array of novel elliptical humeral head prosthesis components where each prosthesis component in the array has a convex articulation surface that is hemielliptical. This hemielliptical surface is defined by a major axis, a minor axis, an apex, and a base having an elliptical cross sectional shape defined by a major diameter along the major axis and a minor diameter along the minor axis. Within the array, each prosthesis component is characterized by a ratio relationship of the minor diameter divided by the major diameter of the base.

Referring again to the drawings, FIG. 1 shows frontal, sagittal and horizontal (transverse) planes relative to a human body and establishes the planes in relation to features of the arthroplasty components as described herein. Generally, the novel arrays of humeral heads herein are characterized by having a diameter in the major axis (DF—corresponding to the frontal plane which transects the joint from superior to inferior) and a diameter in the minor axis (DS—corresponding to the sagittal plane which transects the joint from anterior to posterior), where the difference between the diameter on the major axis minus the minor axis (DF-DS) varies as the measurement DF increases. As further provided herein and as set forth in the claims, the inventors have described formulae for the novel humeral head array. And as further provided herein and set forth in the claims, the inventors have described other features of relationships between DF and DS, and the radii of curvature.

According to the various embodiments, provided herein are humeral head prostheses and arrays, wherein a prosthesis selected from the array based on a patient's DF measurement would have a 97% likelihood of having a 3 mm or less deviation from the size and position of the articular surface at the base of the prosthetic humeral head relative to the patient's normal anatomy.

Referring now to FIG. 2, the upper portion shows alternate views of a humerus shown at the bone cut after removal of the anatomical humeral head. The critical point (CP) and the distal articular mid-point (DAM) are identified before the virtual humeral head resection while determining the humeral head equator as described in the literature by Hertel. After humeral head resection, the length of the diameter of the base of the humeral head in the frontal plane (DF) can be measured as the shortest distance between CP and DAM. DS (the length of the diameter of the base of the humeral head in the sagittal plane) bisects and is perpendicular to DF.DF.DS, and the distance between the bicipital sulcus and critical point (S/E) were identified and measured directly on 3D computer models of humerii.

Referring again to FIG. 2 in the lower portion is an image of an elliptically shaped prosthetic humeral head shown together with formulae that describe the features and relationships there between of a natural humeral head. Using the formulae, for any given value of the diameter of the humeral head in the frontal plane (DF—from superior to inferior—dashed black line), the inventors surprisingly discovered through a study of a large number of humeral heads that one may calculate the values of the other humeral head dimensions, including the diameter of the humeral head in the sagittal plane (DS—from anterior to posterior—dashed white line), humeral head height (HHH—dashed gray line), radius of curvature in the frontal plane ($ROC^F$—black arc), and radius of curvature in the sagittal plane (ROCS—white arc).

Figure 3:
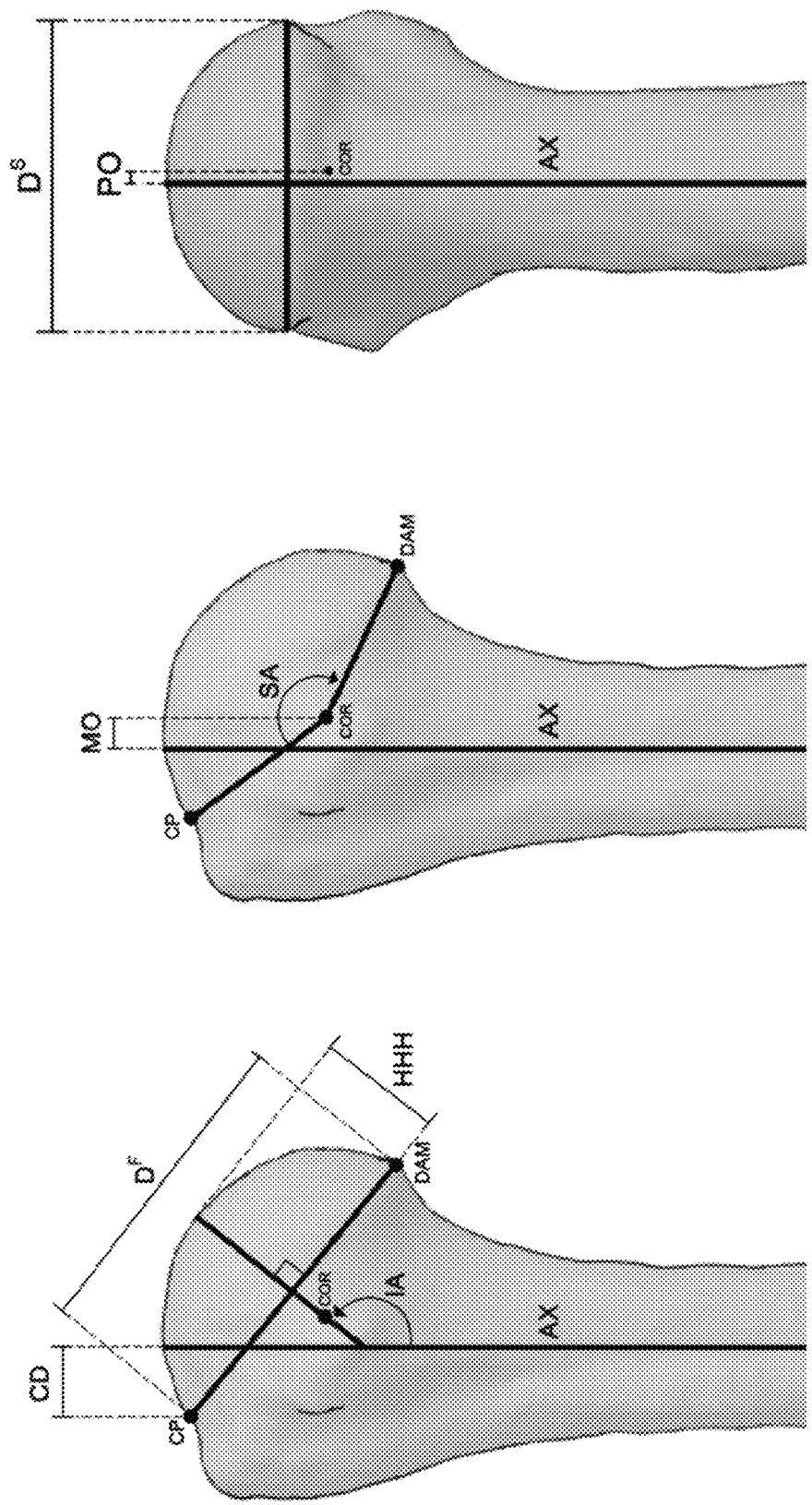
FIG. 3 shows in upper and lower panels alternate front, side and back views of a humerus, indicating key landmarks for determining diameter and radii of curvature to describe the humeral head prosthesis, wherein the lower panel provides stepwise images indicating the steps for characterizing the humeral head prosthesis features as described in the Examples.

Referring again to the drawings, FIG. 3 provides additional details relative to the anatomically relevant markers that were identified in the sample of humerii for providing the parameters and formulae as described herein for elliptical non-spherical humeral head prostheses. FIG. 3 shows anthropometric measurements: AX, long axis of the humerus; CD, critical distance; CP, critical point; COR, center of rotation; DAM, distal articular midpoint; DF, diameter of the base of the humeral head in the frontal plane; DS, diameter of the base of the humeral head in the sagittal plane; HHH, humeral head height; IA, inclination angle; MO, medial offset; PO, posterior offset; SA, surface arc.

Figure 4:
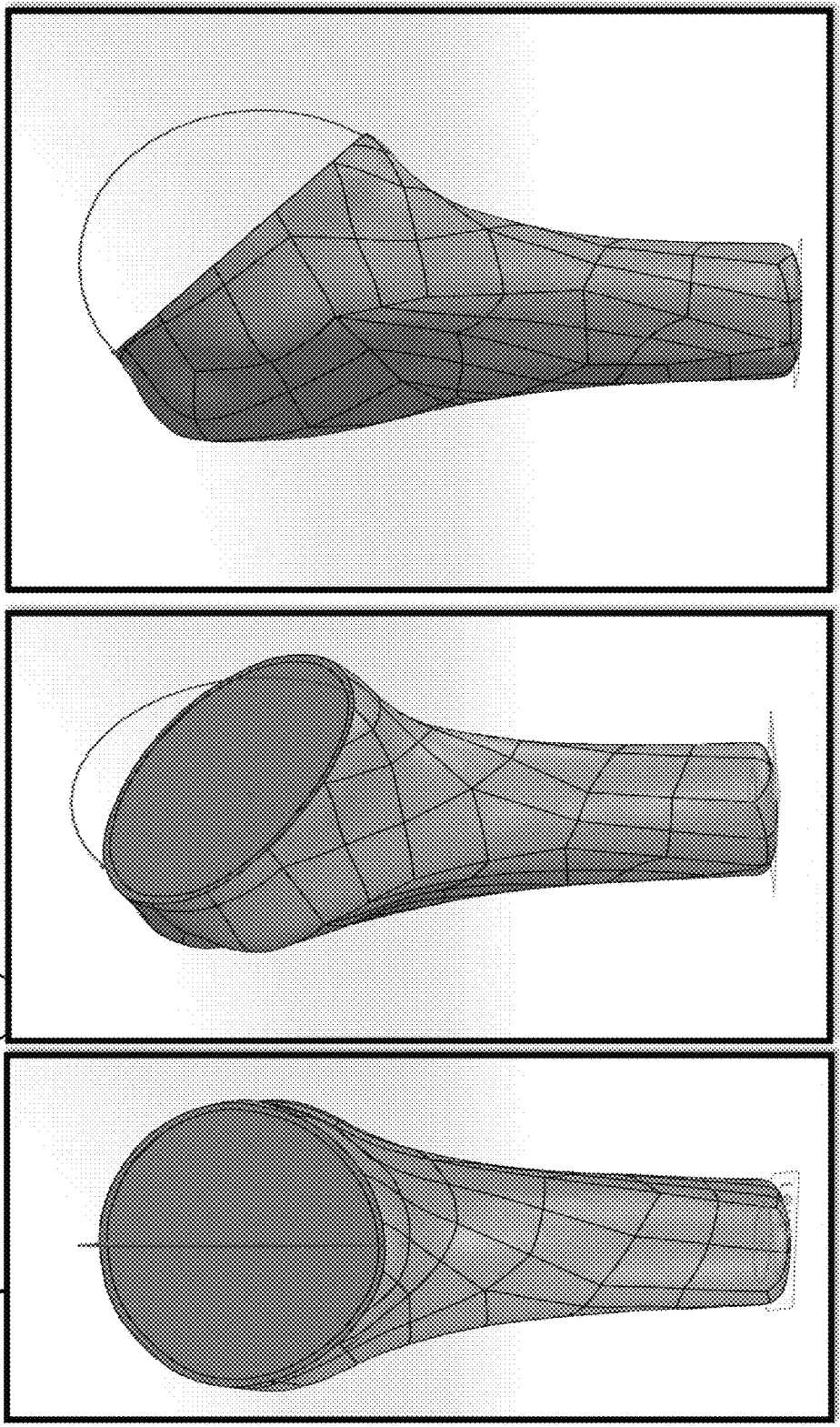
FIG. 4 shows alternate views of a cut humerus indicating the radius of curvature in the frontal plane (SI)
Figure 5:
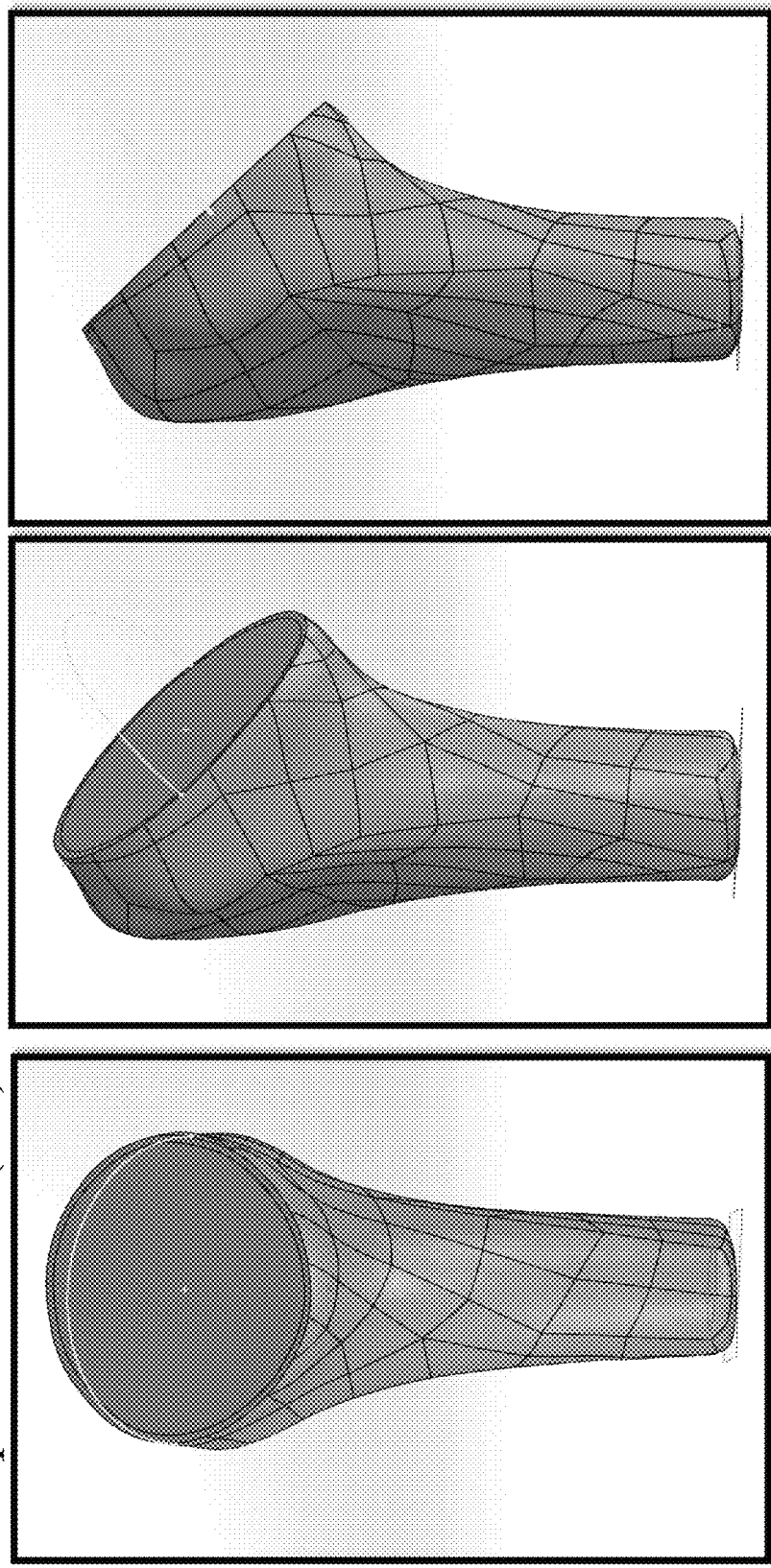
FIG. 5 shows alternate views of a cut humerus indicating the radius of curvature in the sagittal plane (AP)

Referring now to FIG. 4 and FIG. 5, marked simulated radiographs for anthropometric measurement with reference to the anatomical features as shown in the illustrations. The images were produced, whereby (A) To obtain the ideal view for the simulated anterior-posterior radiographs, the humeral head model is oriented so that DF is parallel to while DS is perpendicular to the computer screen. (B) A custom-made ruler with a center slot is used to mark the long axis of the humerus in the frontal plane. (C) Custom-made circular templates that increase in size in 1-mm increments are used to identify the center of rotation and to size the radius of curvature in the frontal plane. (D) Additional lines are added as shown. (E) To obtain the ideal view for the simulated medial-lateral radiographs, the humeral head model is oriented so that DS is parallel to while DF is perpendicular to the computer screen. (F) A custom-made ruler with a center slot is used to mark the long axis of the humerus in the sagittal plane. (G) Custom-made circular templates that increase in size in 1-mm increments are used to identify the center of rotation and to size the radius of curvature in the sagittal plane. (H) Final markup for the simulated medial-lateral radiographs.

Referring again to the drawings, FIG. 4 and FIG. 5, respectively, show the radii of curvature in each of the frontal (SI) and sagittal planes (AP) relative to the bone cut on a humeral head model, corresponding to the approximate location of the humeral head. As further described herein in the Examples, the inventors made the surprising discovery that in a population of individuals, the overall shape and relative proportions of the diameter in each of the frontal and the sagittal planes changes as the overall size increases. As described herein, there are reports in the art that the relative difference between the DF and DS may be typically about 2 mm and up to 4 mm in the context of elliptical humeral heads, which has been treated in the art as a constant variation even as head size increases. What has not been known or suggested in the art heretofore is that this difference between DF and DS is not a constant but varies as head size increases. Accordingly, prosthetic humeral heads that have been designed based upon what has been known have been defective in the relationship between DF and DS relative to native anatomy in at least some populations.

Figure 6:
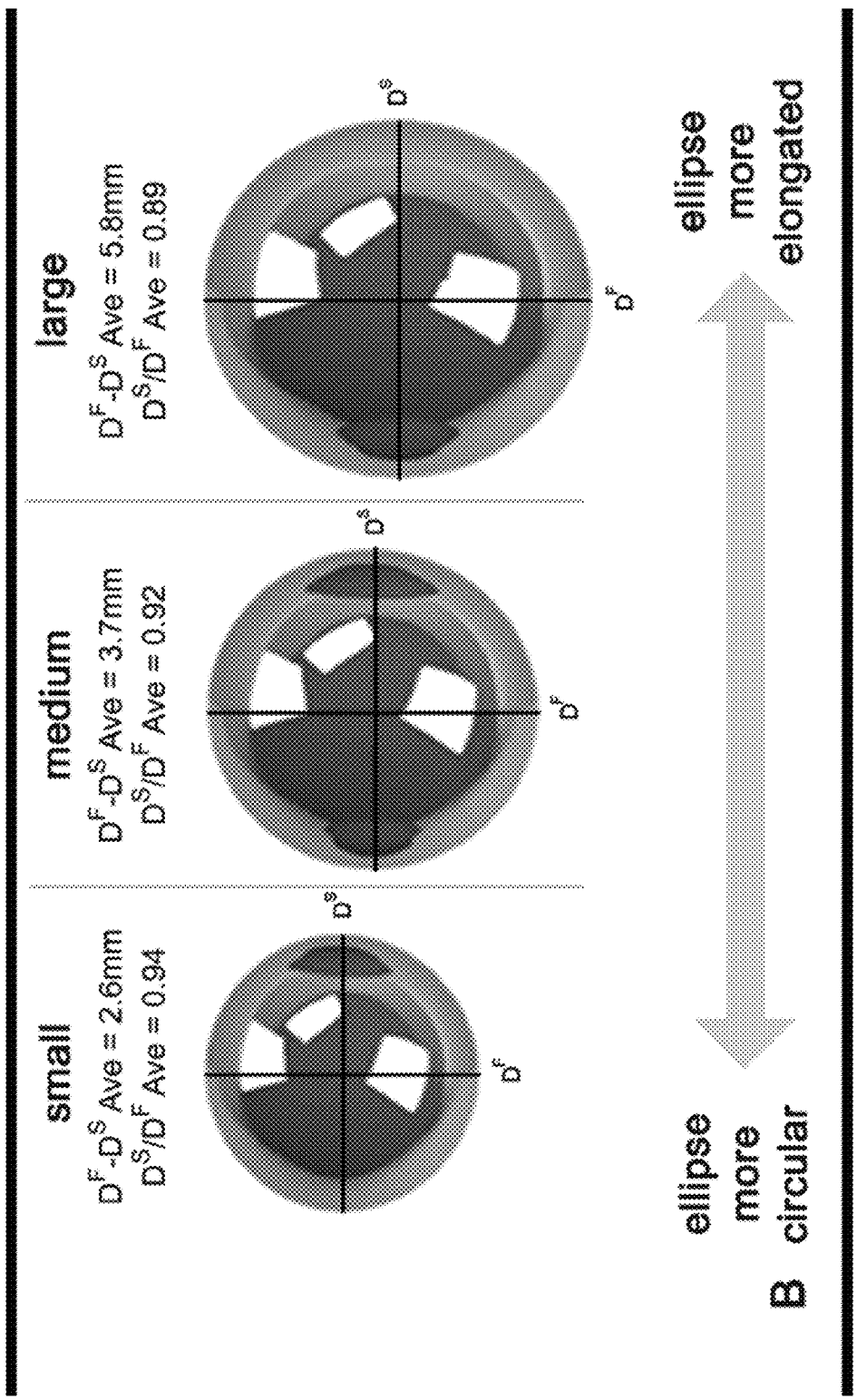
FIG. 6 is a diagram showing variation of the diameter in the frontal plane as humeral size increases.

Referring again to the drawings, FIG. 2 and FIG. 6-FIG. 7 provide details and formulae for the relationships of the features of DF, DS, and HHH and the radii of curvature in the frontal and sagittal planes as size increases overall. Further details are shown in FIG. 16-FIG. 22, which show data and various scatter plots with linear trend lines demonstrating the mathematical relationship between the length difference between the humeral head axes in the frontal and sagittal planes (DF-DS) and the diameter of the base of the humeral head in the frontal plane (DF), and other features of native humeral head anatomy, which data are further illuminated in the Examples. Thus, as shown in FIG. 6, it is possible to described a novel array of elliptical humeral heads based on these surprising findings, wherein as the size increases, the humeral heads change from more circular in cross section to more elliptical (elongate) and the differences between and the ratios of the major (frontal/SI) diameter (DF) and minor (sagittal/AP) diameter (DF) change rather than remain constant.

As described herein, arrays of spherical humeral heads and elliptical humeral heads wherein the measurement DF-DS and the ratio of DS/DF vary as DF increases. In accordance with the various embodiments, the shape of the humeral head prosthesis is generally elliptical (i.e. non-spherical), allowing an enhanced selection to achieve anatomical matching between the removed native humeral head and the prosthesis. In accordance with the disclosure, use of humeral heads that have a non-circular elliptical cross section are particularly desirable for providing the widest array of options to replicate native anatomy and to avoid functional problems for the patient with the arthroplasty.

Assemblies

As described further herein below, use of such humeral heads that have a non-circular elliptical cross section, and in some embodiments used together with a novel coupler component, enables the surgeon to accommodate one or more of offsets in positioning from the sagittal/AP and frontal/SI planes, but also rotational positioning of the humeral heads that have a non-circular elliptical cross section to achieve the most desirable replacement anatomy. Thus, with reference to FIG. 19, it will be evident from the drawings showing a spherical humeral head having a spherical apex (left top and bottom images) or other heads having a spherical apex as compared to those with an elliptical humeral head having an elliptical apex (center top and bottom and right images) that a spherical humeral head that is selected for suitable fit in the DS direction would be undersized in the DF direction (frontal plane), and that a spherical humeral head that is selected for suitable fit in the DF direction would be oversized in the DS direction (sagittal plane), which arrangement could cause rotator cuff tearing and joint stiffness.

In the various embodiments, humeral head prostheses and arrays thereof have dimensions that are suited to allow a range of custom fits to best match a subject's anatomy. As such, humeral heads vary in terms of shape (from more round to elliptical), height (distance from the engagement surface to the apex), and peripheral dimension (circumference for round heads and DS to DF dimensions for elliptical heads). In accordance with what is known in the art, the overall shape of the humeral heads at the apex is generally spherical, though the scope of the invention includes use of humeral heads that may have another shape that is not spherical. In the case of elliptical heads herein, it is contemplated that such humeral heads having spherical apexes would present a glenoid articulation surface that is spherical and would taper along the DF dimensions to the periphery along a generally elliptical arc (ROCF). And in some further embodiments, the head would taper along the DS dimension along a generally elliptical arc (ROCS).

Figure 22:
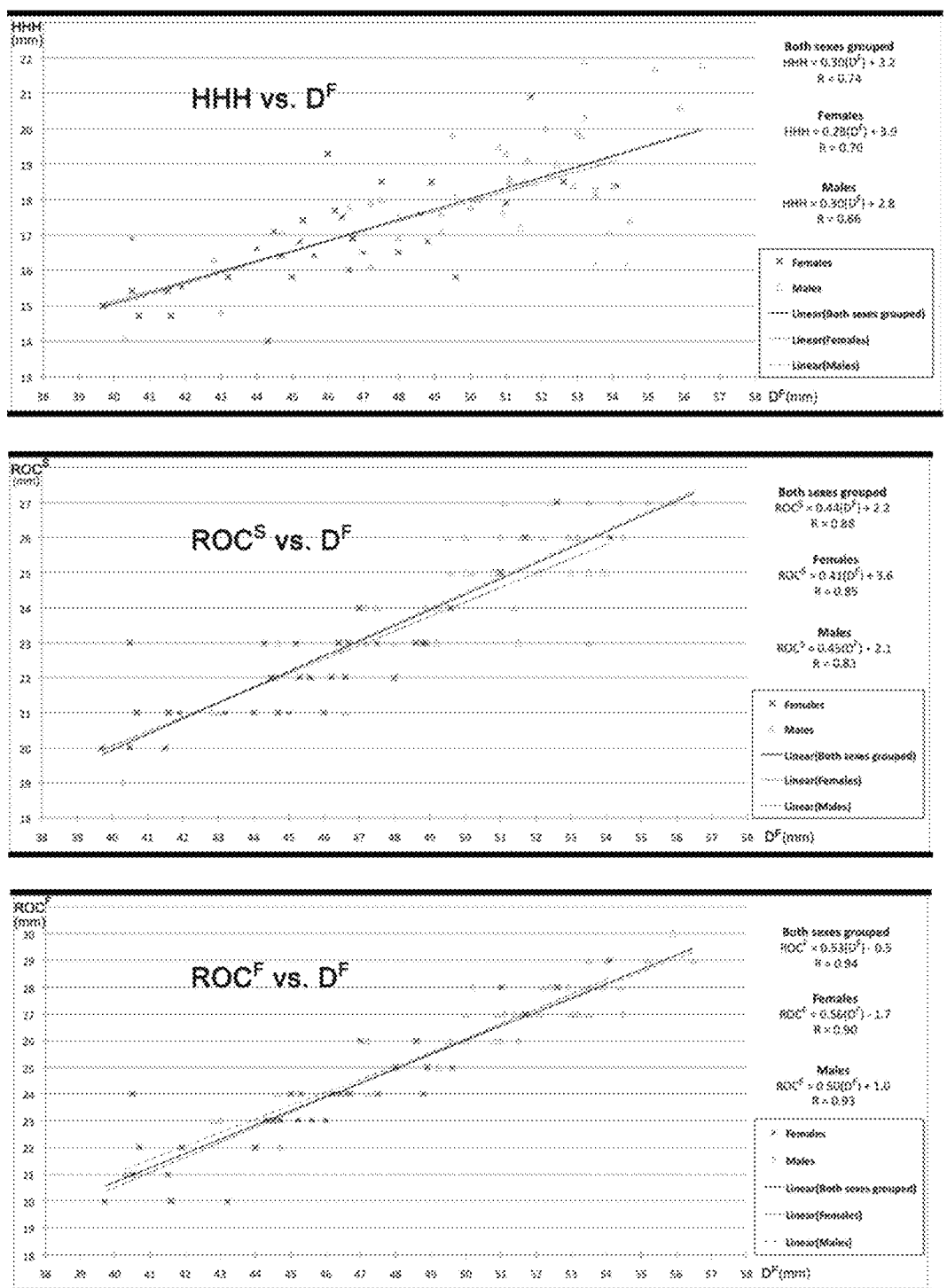
FIG. 22 shows scatter plots with linear trend lines demonstrating in the upper panel graphic the mathematical relationship between the humeral head prosthesis height (HHH) and the diameter of the base of the head in the frontal plane (DF), and in the middle panel graphic the mathematical relationship of the radius of curvature in the sagittal plane (ROCS) vs. DF, and in the lower panel graphic the mathematical relationship of the radius of curvature in the frontal plane (ROCF) vs. DF.

Referring again to the drawings FIG. 20-22, various aspects of the relationships of anatomical humeral heads are shown which inform the described humeral head prostheses and arrays hereof.

Referring now to FIG. 20 the graphic in the upper panel of reveals that for smaller head sizes (DF<45 mm), the difference between DF and DS measurements is always less than or equal to about 4 mm, but once DF increases to beyond 52 mm, the difference is always >4 mm. Taking this into account, the effect of the mismatch seen with use of a spherical prosthetic head is more likely to be of consequence in patients with larger humeral heads because the patient's size variation is not accounted for by the prosthesis shape, thus the size and position of the articular surface at the base of the prosthetic head will be well outside of the goal of achieving a 3 mm or less deviation from normal anatomy. Referring again to the drawings, the graphic in the lower panel of FIG. 20 compares the formula from the inventors' anatomical study, reported below, versus spherical heads, versus heads with a fixed 4 mm DF and DS difference (DF-DS). The shaded grey area is the data plot from the population study+/−3 mm.

Referring now to FIG. 21 upper panel graphic, the shortcomings of the spherical head design are obvious. The spherical size remains within this +/−3 mm goal range only for the smallest individuals; if the DS measurement were used in sizing a spherically shaped humeral head during arthroplasty surgery, the mismatch in the DF direction would be at most 4 mm for a smaller patient; but in larger patients, the mismatch would be 4 mm at a minimum, and it could be >9 mm in some patients. And with respect to elliptical heads having a fixed 4 mm DF and DS difference, referring now to FIG. 21 lower panel graphic, the deviation falls within the +/−3 mm goal range for mid-sized heads, but not for large or small patients. Similar results would be expected for elliptical humeral heads having a fixed 2 mm DF-DS offsets. Based on the data, such humeral heads would capture more patients than spherical heads, but fewer than 4 mm fixed heads. Based on the data shown in the lower panel graphic of FIG. 13, about 76% of patients receiving spherical heads and about 18% of receiving humeral heads where the measurement DF-DS is fixed at 4 mm would likely have mismatch in the size and position of the articular surface at the base of the head of greater than 3 mm. For those patients receiving either spherical heads or fixed 4 mm DF-DS heads with deviations of more than +/−3 mm, the clinical outcomes would likely be compromised. Thus, the inventors have shown that the humeral head prosthesis designs currently known in the art present less than ideal matching to native patient anatomy, both in the case of spherical humeral heads and elliptical humeral heads having constant DF-DS offsets of about 2 mm to about 4 mm.

In various embodiments, humeral head prostheses and arrays of humeral head prosthesis components are provided, wherein each prosthesis component in the array has a convex articulation surface that is hemi-elliptical and defined by a major axis, a minor axis, an apex, and a base having an elliptical cross sectional shape defined by a major diameter along the major axis and a minor diameter along the minor axis. Each prosthesis component in the array is characterized by a ratio relationship of the minor diameter divided by the major diameter of the base, each having a major diameter and a minor diameter that is different from each of the other prosthesis components in the array, wherein as the major diameter is increased the ratio of the minor diameter to the major diameter is decreased. The humeral head prosthesis components in the array vary from having a base with a more circular cross sectional shape to a more elongated elliptical cross sectional shape with increasing size.

As described herein, the DF and DS dimensions of a humeral head according to the disclosure are in reference to a cross sectional plane of a humerus essentially in the DS plane with an inclination angle off that plane from about 120 to 145 degrees, and in some embodiments from 120 to 143, and in certain disclosed embodiments herein, of about 135 degrees. The cut corresponds to the anatomical neck of the humerus as depicted, for example, in FIG. 3, and also see URL (//en.wikipedia.org/wiki/Anatomical_neck_of_humerus).

In accordance with the various embodiments, the humeral head prosthesis may be provided for implantation at an angle of inclination from and including angle increments in between 120, 121, 122, 123, 124, 125, 126, 127, 128, 129, 130, 131, 132, 133, 134, 135, 136, 137, 138, 139, 140, 141, 142, 143, 144, and 145. Thus, in accordance with the disclosure, in various embodiments, stems and other arthroplasty components are provided for engagement with a humeral head prosthesis having an inclination that is about 135 degrees, or otherwise as provided herein. It will be apparent to one of ordinary skill in the art that the stems could be provided having a different angle of inclination, and that the ultimate angle of inclination of an implant is determined based on the angle selected by the surgeon when selecting the prosthesis components to provide an optimally anatomical match to the patient.

Referring again to the drawings, FIG. 7 shows an exemplary elliptical head that has a size as described by its major and minor axes, dimensions and radii of curvature. In accordance with the various prostheses in the disclosed arrays, the heads vary in size relative to a bone cut on the DS plane. In one representative embodiment of an array of elliptical heads, arrays can be described as follows, where each prosthesis in the array have diameter dimensions that range from 30 mm to 62 mm in the superior to inferior dimension (DF), and range from 30 to 58 mm in the anterior to posterior dimension (DS). In some particular embodiments, the DF range is from 37 to 56 mm and the DS range is from 36 to 51 mm. In yet other embodiments, the DF range can encompass from 20 to 80 mm, and can include sizes in the DF dimension from and including the following and increments in between: 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80 mm. Likewise, in such other embodiments, the DS range can encompass from 20 to 80 mm, and can include sizes in the DS dimension from and including the following and increments in between: 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80 mm. Selection of the specific size based on DF and or DS will be made in accordance with the skill in the art and with particular reference to the size and population features of the subject in accordance with the teachings herein. Thus, the arrays and the discrete prostheses will have elliptical head properties in accordance with one or more of the formulae and DS to DF relationships as described herein.

In one representative embodiment of an array of elliptical heads, included humeral head sizes that may encompass the following array, wherein the DS dimension ranges from 36 to 51 mm, the DF dimension ranges from 37-56 mm, the ratio of DS/DF ranges from 0.87 to 1, and wherein the angle of inclination ranges from 120 degrees to 143 degrees. Specific humeral heads within the array are provided in sizes having humeral head heights ranging from 12 to 25 mm, and in representative embodiments from 14 to 21 mm, and in certain specific embodiments in increments there between.

Referring again to FIG. 2, the relationship between the DF to DS dimensions in one embodiment of elliptical heads is 1 (spherical heads). In some embodiments according to the disclosure, the DF to DS dimensions are related in a range where the DF dimension is about 2 mm larger than the DS dimension regardless of head size. In alternate embodiments, the variation between the DF and DS dimensions may vary from 0.5 mm to 10 mm or more, and thus can include variation in mm and increments in between including 0.5, 1, 2, 3, 4, 5, 6, 7, 8, 9, 10 mm. In yet another alternate embodiment, the DF to DS dimensions are related in a range where the DS/DF ratio changes from 1 to 0.85 as the head size and DF increases. Generally, according to such embodiments where the DS/DF ratio changes, the range in variation between the DF and DS dimensions can include from 0.5, 0.6, 0.7, 0.8, 0.9, 1, 1.5, and 2 mm and incremental fractions there between.

Coupler Components (Metaphyseal Shell)

In some embodiments, the elliptical humeral heads may be used together with a coupler/metaphyseal shell that is engageable with a prosthesis component, for example an elliptical humeral head prosthesis component, according to the disclosures to provide an arthroplasty assembly. FIG. 8-FIG. 10 show alternate views of systems that comprise prostheses components and one or more of anchors and couplers in the context of bony anatomy. In particular, FIG. 10 shows optional components of an assembly for long bone arthroplasty, the assembly including one or more elliptical head prostheses, and one or more of coupler and anchor prostheses. In some particular embodiments of assemblies, one or more alternate anchors selected from stems and cages (see FIG. 10 and FIG. 11) may be included, and the assemblies may contain spherical heads and cup shaped prostheses (see for example FIG. 11 and FIG. 8), each of the various prostheses inter-engageable with a coupler component to maximize the options for a surgeon and to provide a system that is adaptable for revision without the need to remove the entire implant, particularly when a coupler component is used, with or without any anchor (examples with and without anchors shown in FIG. 8).

Figure 15:
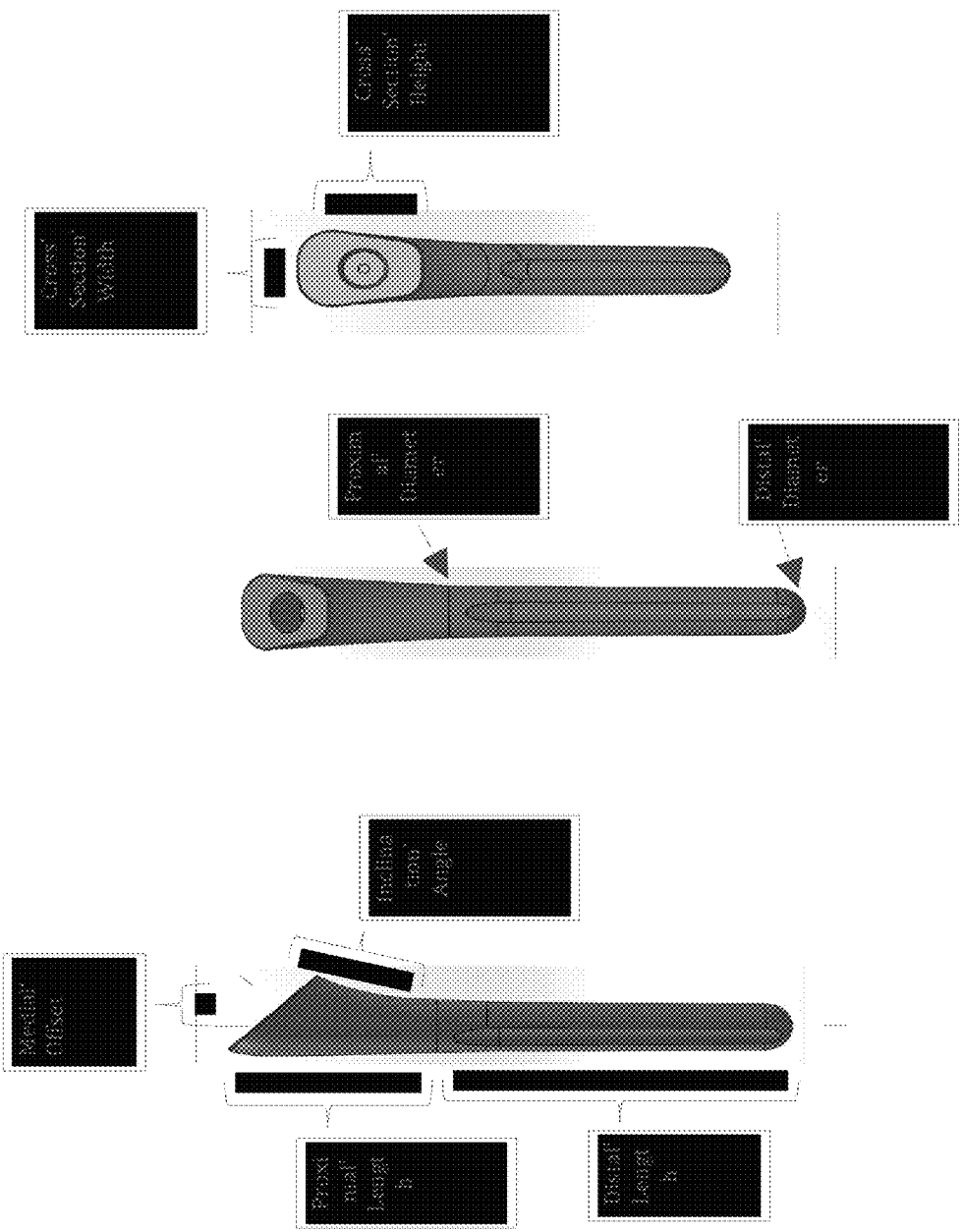
FIG. 15 shows alternate side, front and front cross-sectional views of a representative embodiment of a diaphyseal stem.
Figure 19:
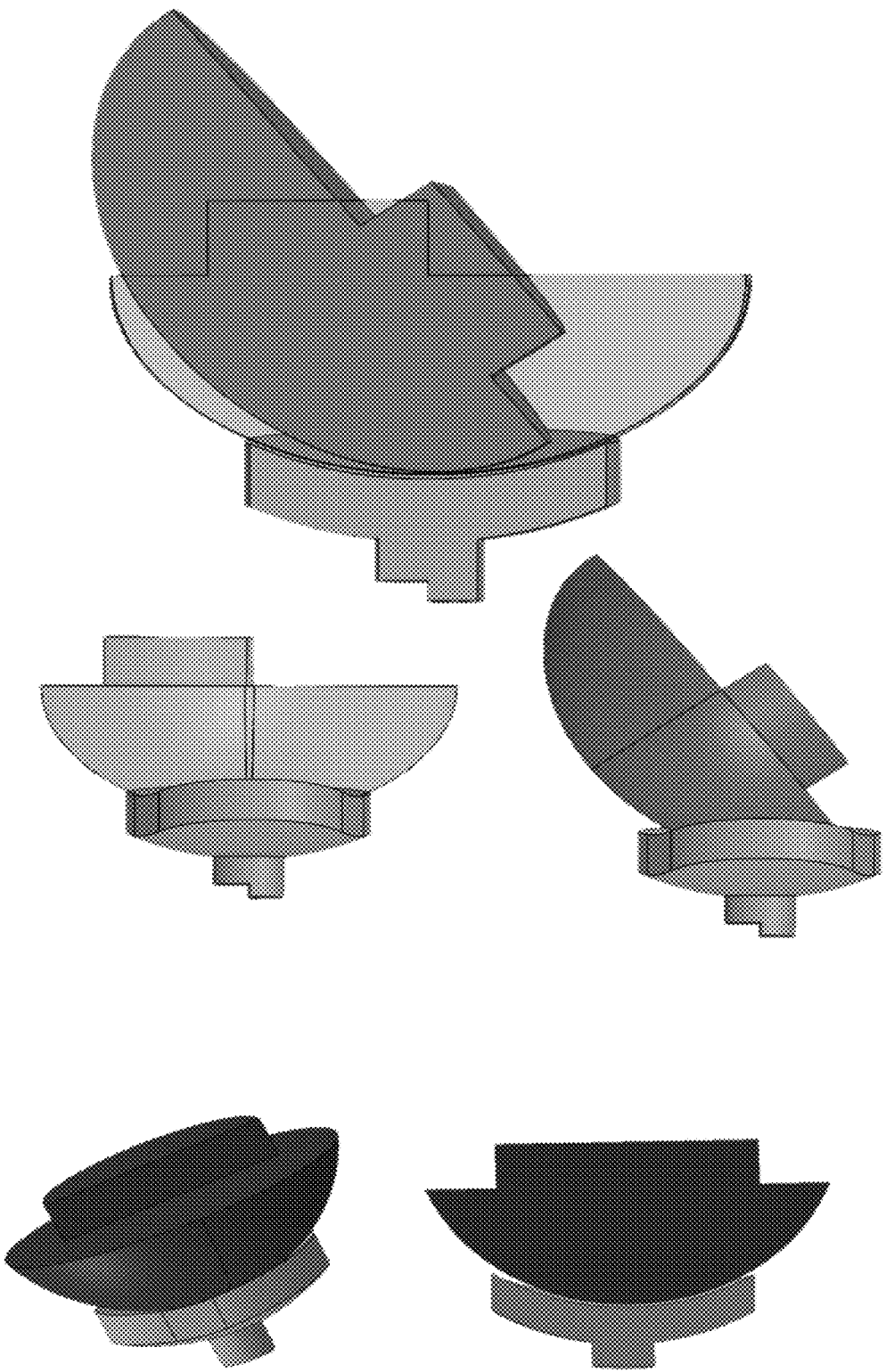
FIG. 19 shows alternate views of the articulation of a spherical vs. an elliptical humeral head prosthesis relative to a glenoid.

Referring again to the drawings, FIG. 8 shows alternate perspective views of various embodiments of a modular arthroplasty assembly with a coupler component. FIG. 15 depicts alternate views of an exemplary anchor that may be used, the anchor comprising an elongate stem and a contact surface comprising an engagement feature in the form of a female taper for engagement with one of a coupler component and a prostheses component.

In some embodiments, the coupler when used with an anchor, enables variable positioning of the prosthesis component relative to the long axis of the bone, assembled in the context of a shoulder bone. Using the coupler of the modular system, the position of the prosthesis component can be varied rotationally around a shared central engagement axis with the coupler component to allow for selection of the optimal anatomical positioning of the elliptical humeral head. According to those embodiments that include an anchor, a position of the anchor component relative to the coupler component can be varied in two dimensions on a plane that is perpendicular to the central engagement axis of the coupler and prosthesis components by selecting the coupler component from an array comprising a plurality of coupler components that include variably positioned anchor engagement features.

Accordingly, provided in some embodiments, a modular arthroplasty assembly includes the components of: (a) an elliptical head selected from an array as described above and (b) a convertible coupler bounded on a first side by an implant surface adapted to receive an implant component, and bounded on an opposite second side by a bone contact surface. In some embodiments, the assembly may also include one or more of an array of prosthesis components that are selected from one of a hemispherical humeral head and a cupped reverse prosthesis. In yet other embodiments, the assembly may include an anchor.

Figure 14:
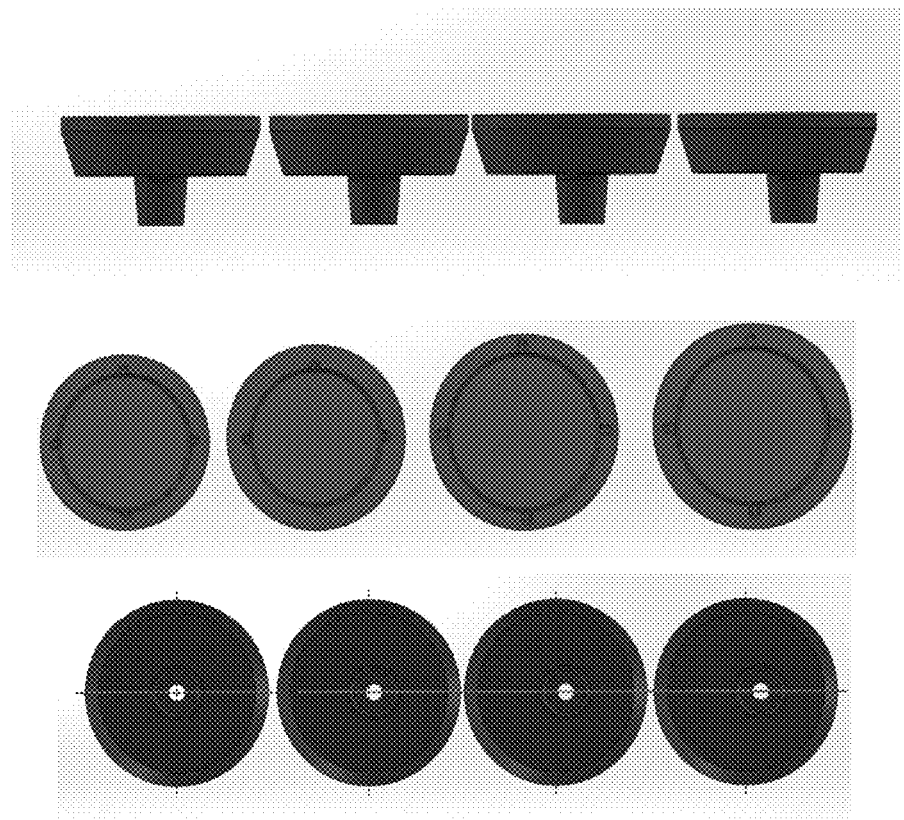
FIG. 14 shows an array of sizes of a representative embodiment of a coupler/metaphyseal shell shown from the side, the top and the bottom.

In accordance with the invention, with reference for example to FIG. 13 and FIG. 14, each of at least two of the plurality of coupler components comprises at least one anchor engagement feature that is off-center from a center point of the coupler component, and the off-center engagement feature on each of the at least two coupler components is at a different distance in at least one dimension that is perpendicular to the central engagement axis. In use, when the coupler and anchor components are recessed into bone, the assembly achieves alignment of the bone articulation surface of the prosthesis component with the bone that is anatomically similar to a native long bone.

Thus, in some embodiments, a modular arthroplasty assembly includes (a) an convertible offset coupler bounded on a first side by an implant surface adapted to receive an implant component, and bounded on an opposite second side by a bone anchor engagement surface, (b) an elliptical non spherical humeral head prosthesis component, and optionally, (c) a bone anchor configured to be inserted in bone and adapted for engagement with the convertible offset coupler.

In use, the concentric coupling feature on the humeral head prostheses provides a superior solution for use of elliptical heads to achieve an optimized anatomical match and is a key aspect of the novel system disclosed herein to allow anatomical matching for up to 97% of patients (based on the study data reported in the Examples herein). Rotational orientation occurs at the humeral head prosthesis-coupler engagement interface, while offset occurs at the coupler/anchor engagement interface. Selection from the arrays of heads, shells and anchors, as further described herein below, and surgeon selected orientation of the rotational position of the elliptical articulation surface, followed by final fixation of the assembly, allows creation of a near match to the patient's native anatomy. Moreover, because of the modularity of the components, any surgical revision that may be necessitated can be more easily achieved than is currently possible in the art by use of the coupler, which allows positional adjustment, replacement, removal and replacement of the head with a cup to achieve a reverse arthroplasty, all without the need for complete removal of the shell/anchor implant from the humerus.

In various embodiments, referring now to FIG. 11-FIG. 14, the overall shape of the coupler is generally cylindrical, with an outer surface and dimensions that are adapted for insertion at least partially within humeral bone and is bounded on a first side by an implant surface adapted to receive an implant component, and on an opposite second side by a bone anchor engagement surface. In some embodiments, for example as shown in FIG. 11 and FIG. 13, the coupler is adapted with at least or one another of a male insert and a female receiver channel (such as a Morse type taper), on one or both opposing sides, and optionally adapted to receive one or more of a pin or setscrew or other fastener to achieve engagement with at least one of the prosthesis component and the bone anchor. In some embodiments, the coupler bears on a lateral peripheral edge a surface feature that is adapted to enhancing boney ingrowth. Accordingly, in some embodiments, all or a portion of the outer surface of the coupler may be adapted with surface texturing to encourage bone ingrowth or ongrowth. In addition, the stem engagement surface may be adapted with surface texturing to enhance engagement there between. In various embodiments, the coupler includes at least one engagement feature that allows engagement and fixation with each of the humeral head and cup prostheses.

Referring now to FIG. 14, the coupler component is shown in an array of sizes of a representative embodiment with side, top and bottom views in each of the top, middle and bottom panels, respectively, whereby the position of the anchor engagement feature may vary to provide an array of shells for selection to provide a customized fit and engagement for a humeral head or cup prosthesis. In the various embodiments, a coupler with an offset for engagement with an anchor is selected from offsets ranging in mm and increments thereof from 0 to 20 mm, and includes 0, 1, 2, 3, 4, 5, 6, 7, 8, 9, 10, 11, 12, 13, 14, 15, 16, 17, 18, 19, and 20. In some representative embodiments, the range of offset may be from 0 to 10, and in some specific embodiments, the offset may be from 0 to 6 mm.

Referring again to FIG. 14, the exemplary set of couplers may be characterized as representing offsets of 0, 1, 2, and 3 mm. In accordance with the representative array, the couplers may vary in diameter from about 30 to 45 mm, more particularly from 34 to 40 mm, and in some specific embodiments include sizes that are 34, 36, 38 and 40 mm in diameter, respectively. Of course other sizes and incremental portions thereof are possible, and can range from 5 mm to more than 100 mm in diameter depending on the subject. Thus, couplers may be provided in heights ranging in mm increments and fractions thereof from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to 100, and in diameters in mm increments and fractions thereof from 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to 100.

It will be appreciated that any range of offsets may be provided, and that series of offsets on couplers of different diameters and heights, as described herein below, may be provided. In use, in a representative example of a modular arthroplasty system, as depicted in the drawings, a coupler is selected for its height, diameter, and engagement feature offset using tools for offset measurement as described further herein below. The selected coupler is placed in the bone, its male taper engaged with the female taper of the stem; a set screw is inserted through the taper to engage the coupler with the stem to secure the implant system in preparation for engagement with the humeral head or cup prosthesis.

In some particular embodiments according to the disclosure, a modular system for long bone arthroplasty is provided. The modular system includes an elliptical humeral head prosthesis, an anchor component, the humeral head prosthesis component engageable with the anchor component to provide an arthroplasty assembly, wherein the position of the humeral head prosthesis component can be varied rotationally around a shared engagement axis with the anchor component.

In the various embodiments, this coupler is positioned by countersinking in bone, such as the cut humeral head bone in the case of shoulder arthroplasty, in a region that is proximate to or within the metaphysis (wide portion of the long bone between the epiphysis—head—and the diaphysis—the shaft). In other embodiments, this coupler may be positioned partially within the bone or on the cut surface of the bone for cases in which achieving anatomical match in a patient necessitates increased height on the superior aspect of the humerus.

Humeral Stem Component

Referring again to the drawings, FIG. 15 show a variety of views of representative bone anchors in the form of diaphyseal stems in accordance with the disclosure. In various embodiments, the depicted shoulder prosthesis humeral stems are adapted for engagement with a coupler/metaphyseal shell. The humeral stem component may be used with the various modular adapter components described herein in the manner described above to configure humeral stem with broad flexibility for relative positioning of the metaphyseal shell and prosthesis component relative to the stem.

Referring again to FIG. 15 which shows alternate views of an embodiment of a diaphyseal stem, the stem is comprised of a proximal region (about the upper ⅓ of the stem) that is adapted for alignment with the bone cut in the metaphysis and engagement to the shell, and a distal region (about the lower ⅔ of the stem) which is fit into the distal region of the diaphysis. In various embodiments, the shape of one or both the proximal and distal ends of the stem are adapted to be press-fit within the bone. In certain exemplary embodiments, the proximal portion of the stem is selected to be a best fit for tight press-fit within the upper diaphysis/metaphysis of the bone. In various embodiments, the humeral stem includes an engagement feature, which is shown in representative FIG. 15 as a female taper receiver on its proximal end that is adapted to receive a male insert, such as a tapered extension, to achieve engagement with the metaphyseal shell. In some embodiments, the size, shape, location/position of the receiver and combinations of these features may vary to allow adaptability to the relative positioning of the engaged stem and metaphyseal shell. Overall, the cross-sectional shape of the stem at its proximal end is generally trapezoidal and is adapted for achieving a desirable degree of fill of the upper end of the diaphysis and the metaphysis. In various embodiments, based on the size of the stem, the degree of fill to be achieved with a stem ranges from 20 to 60%, and in some desirable embodiments about 40%. Thus, the extent of fill ranges from and includes as a percentage of the void space in the engagement area of the bone, about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, to 60. Overall, the cross-sectional shape of the stem at its distal end is generally circular and may be adapted with fluting or other features to facilitate engagement of instruments for ease of removal as needed.

In some embodiments, the stem component is adapted to enhance bony ingrowth and bone strength at regions of the humeral bone, for example at the proximal end only of the stem. Surface features on the proximal and distal end may be included in some embodiments to facilitate fixation in the bone and facilitate subsequent removal, as in the instance of revision surgery. According to some embodiments, the surface of the stem is configured with features and surface texturing to encourage bone growth along the proximal end of the stem, and the tapered distal end is devoid of texturing to discourage bone ingrowth and to enable easy disengagement of the stem from the distal diaphyseal portion in the event removal is necessary. In some embodiments, the entire lateral surface of the proximal end is textured to encourage bone ingrowth. In alternate embodiments, the stem has flattened panels on its sides and the flat areas of the proximal end are textured for bony ingrowth while the remainder of the lateral portions of the proximal end are not textured.

the length of the stem may be varied, and its proximal and distal dimensions and features may likewise be varied in accordance with those known in the art. In some embodiments of stem arrays, the girth of each stem size grows proportionally as the size increases, and the proximal and distal sections grow incrementally with size, with the distal length increasing at a greater rate relative to the proximal length. It will be apparent to one of ordinary skill that varying shapes and sizes of stems are possible and generally within the skill in the art. In the context of the stems disclosed herein, the relative girth of the proximal end is selected to achieve the closest possible press fit within the bone to enhance stabilization, to provide maximal proximal surface contact to support the metaphyseal shell and to accommodate the fixation engagement between the shell and the stem. Thus, variations in stem features are possible with respect to sizing, and the size without departing from the scope of the disclosure and the claims.

Arrays may include the following possible set of stems: short stems that vary in length ranging from about 70 mm to 98 mm; standard stems that have a length of about 125 mm; and long stems that have a length of about 175 mm; Within each of these lengths, the stems further vary in size, with 8 representative sizes. In accordance with the foregoing, in various embodiments, the stems may have length dimensions as follows: The stems may vary in size from small at a length of from 45 to 110 mm, and more particularly from about 60 to 95 mm, and more particularly from about 60 to 95 mm; to a medium length from about 110 to 130 mm, and more particularly from about 125 mm; to a long stem length from about 130 mm to about 180 mm, and more particularly from about 175 mm. In various embodiments, the stems may have proximal length dimensions as follows: The proximal portions of the stems may vary in size from 35 to 60 mm, and more particularly from about 40 to 54 mm. In various embodiments, the stems may have distal length dimensions as follows: The distal portions of the stems may vary in size small distal length of from 25 to 50 mm, and more particularly from about 30 to 44 mm; to a medium distal length from about 70 mm to 90 mm, and more particularly from about 71 mm to about 85 mm; to a long distal stem length from about 120 mm to about 140 mm, and more particularly from about 121 mm to 135 mm. The stems are provided to be suitable for placement within bone and engaged with a shell wherein the bone cut is at an angle of inclination from and including angle increments in between 120, 121, 122, 123, 124, 125, 126, 127, 128, 129, 130, 131, 132, 133, 134, 135, 136, 137, 138, 139, 140, 141, 142, 143, 144, and 145. In accordance with the disclosure, in various embodiments, the stems have a shell-mating surface having an inclination that is about 135 degrees. It will be apparent to one of ordinary skill in the art that the stems could be provided having a different angle of inclination, and that the ultimate angle of inclination of an implant is determined based on the angle selected by the surgeon when making the bone cut.

In various embodiments, the stems may have a cross sectional shape that is generally cylindrical, trapezoidal, rectangular or other, and combinations of these between the proximal and the distal ends.

Advantageous features of the coupler that are described further herein include: on its top or superior (articulation surface facing) side, a seat, such as a recess, that is adapted to accept both humeral head and humeral cup (reverse prosthesis) components. The coupler addresses the mechanical challenge of orientation of spherical and most particularly non-spherical humeral head components using the coupler to achieve any anatomically desired offset in either or both the inferior/superior axis and anterior/posterior to achieve optimal anatomical alignment of the prosthetic articulation surface relative to the humeral bone.

In some embodiments, the coupler includes an eccentric engagement feature on the back or inferior (bone facing) side, such as a standard taper (Morse-taper in some embodiments), that is selected for engagement with a bone stem, plug or cage (selected in size for anatomical match with the metaphyseal/diaphyseal portions of the long bone) to replicate and achieve native or normal humeral posterior and medial offset. Thus, in some embodiments, the coupler is adapted to be recessed in bone in the absence of any stem, cage or plug type anchor and in others it may include a stem, cage or plug or taper feature for enhancing contact within the bone.

It is known in the art and deemed desirable by some to distalize the humerus during a reverse shoulder arthroplasty procedure, putatively because greater height in the humeral implant distalizes the humerus and puts increased tension on the deltoid muscle to compensate for lost rotator cuff function. However, there are clinical and mechanical disadvantages to this distalization. Unfortunately, these disadvantages are not easily avoided with implant systems in the art, particularly in the case of current convertible systems, because of the increased height of the humeral implants from the extension of the stem and other components above the bone cut line of the humerus.

The current disclosure, in various embodiments, provides a modular and convertible arthroplasty system that is low profile, having a substantial reduction of implant height as compared with what is known in the art. These embodiments are desirable for avoidance of distalization, particularly in reverse arthroplasty, enabling the surgeon to avoid mechanical and clinical problems associated with the rotational center of the joint, and enabling the use of other options for achieving soft tissue function to replace the rotator cuff.

Figure 23:
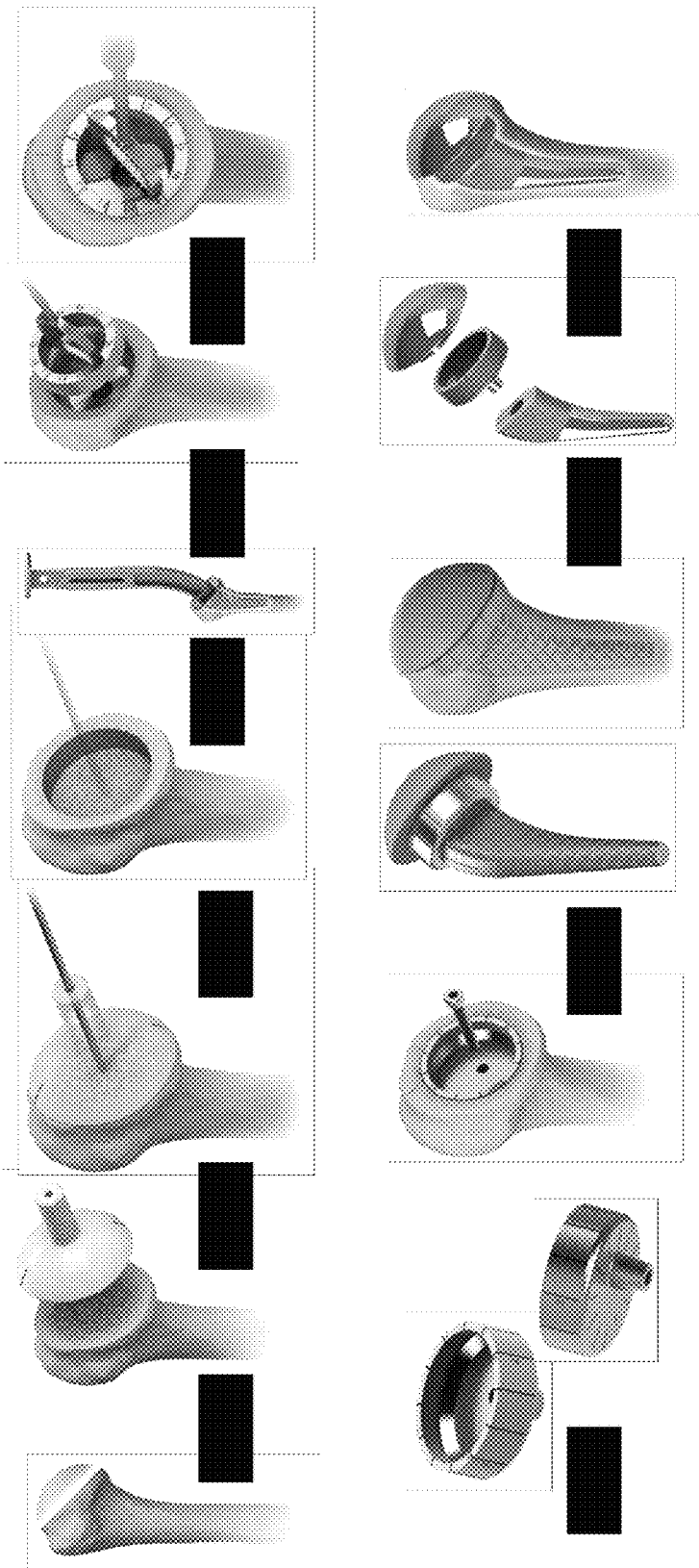
FIG. 23 is a graphic of a step in the sequence of a representative embodiment of a surgical technique for implanting an arthroplasty system in accordance with the disclosure showing a perspective view of a bone cut on a humerus with steps for preparation of the bone to receive a coupler/metaphyseal shell, and steps for selection of the position in the bone of an stemmed anchor, including a stem trial and representative shell offset selection tool for positioning an offset of a prosthesis component relative to the bone.

In some embodiments, the disclosure provides methods for implanting an arthroplasty system. As represented in FIG. 23, the methods include selecting from among at least prostheses components and one or more of coupler and anchor components, establishing at least the orientation of the major and minor axis of elliptical headed prostheses, and optionally any offset thereof relative to an anchor, and prepping and implanting one or more of a coupler and anchor prior to affixing and orienting the prosthesis. The methods embody examples wherein a cup shaped prosthesis is initially or after a revision surgery affixed to a coupler component implanted by at least partial countersinking in the bone. In various embodiments, the surgical method for implanting a system comprising at least a coupler component and a prostheses component, and optionally an anchor involves access to the proximal humerus bone for removal of the native humeral head and replacement with a modular arthroplasty assembly in accordance with the disclosure. Referring again to FIG. 23, a graphic depiction is provided of steps for implanting an arthroplasty system in accordance with the disclosure.

The specific order of the steps outlined herein below are not intended to be limiting, and not only may the order be varied, but additional steps may be included, and certain steps may be eliminated based on the specifics of the anatomy and other factors.

For example, according to embodiments in which an anchor is not used, then the steps for use of a trial for an anchor and for prepping the bone to receive an anchor may be eliminated, as well as the steps of determining offset of the prosthesis from a center point of an axis of an anchor.

According to embodiments in which no anchor is used, or where only a cage or plug that is centered on the coupler is used, then no offset is required. In yet other examples, where no coupler is used and only an anchor, such as a stem is used with a prosthesis, no offset is required beyond selecting an anchor and implanting it with a desired angulation relative to the long bone and an axis oriented relative to the long bone.

The humeral head is surgically accessed; the anatomical neck of the humerus is cut (for example, at approximately 135 degrees based on the native anatomy, or at such other angle as may be determined by the surgeon with or without a cut guide) and the native humeral head is removed; a trial humeral head "sizer" or guide is positioned on the proximal humerus bone cut, the sizer being anatomically shaped like the intended prosthesis heads; the desired size and orientation are determined; the trial head sizer will have a central hole in it; after proper size and orientation of trial humeral head have been determined, the sizer is fixed in place and a pin is drilled through the center hole in the sizer; the sizer head is removed from over the pin, leaving the pin in place (a K-wire may be used); a reamer that is size dimensioned to match the size and shape of the metaphyseal shell is selected and placed over the central pin (for example, the size of the metaphyseal shell and corresponding reamer is selected from a set of reamers with dimensions ranging from 30 to 60 mm); the reamer is operated to form a recess cavity in the bone to accommodate the metaphyseal shell (the "metaphyseal shell seat"); optionally, a broach/trial prostheses for the humeral stem is selected to find the axis of the diaphysis; starting with the smaller diameter broaches, the bone is trialed and the broaches exchanged for those increasing in size until a trial is identified that provides a snug fit; the trial broaches will be shaped like the diaphyseal portion of the humeral stem portion of the implant; optionally, an alternate or second broach/trial for the stem is selected to determine stabilizer size, shape and length to most closely match the anatomy; starting with the smaller diameter stabilizer broaches, the bone is trialed and the broaches exchanged for those increasing in size until a trial is identified that provides a snug fit distally and to a depth that is desirable for the humeral stem portion of the implant; optionally, feature such as a graduated line or plate or other indicator on the broach handle is used to determine the depth of the broach to achieve alignment of the proximal end of the stem with the bottom of the metaphyseal shell recess (i.e., alignment of the top/proximal surface of the stem with the surface line of the bone in the metaphyseal shell seat); once a snug fit has been achieved, the broach handle is removed; the desired broach depth will provide positioning of the location of the female taper of the broach/trial stem, and a correspondingly sized trial stem is inserted in the bone, and a size guide is positioned over the metaphyseal shell bone cut to determine offset positioning for the male taper of the metaphyseal shell with the female channel of the stem; a coupler/metaphyseal shell, optionally with the appropriate offset for engagement with the stem is selected (offset examples include 0, 2, 4, or 6 mm of offset) and placed in the bone, its male taper engaged with the female taper of the stem; a screw is inserted or another coupling device is utilized to engage the trial metaphyseal shell with the broach/trial stem to complete the trial implant system; a trial prosthesis is selected, such as from a humeral head or reverse arthroplasty cup prostheses; the trial implant is removed, the screw or other coupling device will have locked the orientation of the metaphyseal shell relative to the stem and indicators on the metaphyseal shell (for example, numbered 1-12 to indicate position, like the face of a clock) will provide a key for the surgeon as to how to assemble the final components for implantation (e.g., from the trial components an indicator #3 on the metaphyseal shell may align with a particular marker indicator on the proximal end of the stem, so the final component is then assembled to match these indicators), using the sizes of metaphyseal shell and stems as selected with the trials with a predetermined size enhancement (dimensions slightly greater than the trial, as predetermined) to ensure a tight press fit into the bone; the full implant is assembled on the bench, and then press fit into the bone such that all or substantially the entire metaphyseal shell is below the bone surface, and so that all or substantially the entire stem is below the bone surface at the base of the metaphyseal shell seat.

It will be appreciated that the above technique may be varied, and that the components described are merely exemplary, and features size as engagement means, as well as dimensions, and engagement indicators and gauges may be varied, and are thus non-limiting.

Further, in accordance with some exemplary embodiments, the countersunk position of the coupler below the bone cut allows the surgeon to achieve a more anatomical configuration than other systems can achieve at time of primary or revision surgery. In particular, the position and features of the coupler enable substitution of articulation surface prostheses, and as needed, removal of the shell during a revision. In some embodiments, removal of the shell enables replacement with a shell having an alternate offset to enable maximum flexibility for achieving desired anatomical structure in a revision surgery.

To facilitate removal from bone, the coupler has a lateral edge that is in some exemplary embodiments roughened or porous coated to achieve bony ingrowth for reliable fixation, while the bottom of the coupler is smooth to prevent bony coupling in some embodiments, thus allowing for greater ease of removal from bone should that be necessary in a later procedure. Taking advantage of the convertibility, and ease of selection of head/cup implant components, the coupler allows for minimal bone removal or manipulation at time of revision/conversion. And, as depicted in FIG. 23, the use of the coupler trial with marking features enables precise and virtually unlimited increments of offset adjustability, eliminating need for large inventory of prosthetic heads and cups. The options for adjustability are particularly wide when the coupler is used in combination with a suite of stems that are size and shape adapted for a wide range of patient anatomy.

In some embodiments a modular system for long bone arthroplasty is provided comprising: an array of humeral head prosthesis components, each humeral head prosthesis component in the array having a convex articulation surface that is hemielliptical and defined by a major axis, a minor axis, an apex, and a base having an elliptical cross sectional shape defined by a major diameter along the major axis and a minor diameter along the minor axis, each humeral head prosthesis component in the array characterized by a ratio relationship of the minor diameter divided by the major diameter of the base, the array comprising a plurality of humeral head prosthesis components, each having a major diameter and a minor diameter that is different from each of the other humeral head prosthesis components in the array, wherein as the major diameter is increased the ratio of the minor diameter to the major diameter is decreased, whereby the humeral head prosthesis components vary from having a base with a more circular cross sectional shape to a more elongated elliptical cross sectional shape with increasing size.

In some further embodiments of a modular system, the system further comprises a coupler component selected from an array of coupler components where each coupler component in the array includes a humeral head prosthesis component engagement side and an opposite anchor component engagement side, and has sides bounded by a lateral edge. In the various embodiments, the lateral edge may be one of cylindrical, frustoconical and frustohemispherical, and may have a surface treatment or texturing to encourage bony ingrowth or ongrowth. The array of coupler components is characterized by having variably positioned anchor engagement features where each of at least two of the plurality of coupler components comprises at least one anchor engagement feature that is off-center from a center point the central engagement axis of the coupler component, and wherein the off-center engagement feature on each of the at least two coupler components is at a different distance in at least one dimension that is perpendicular to the central engagement axis. In accordance with such embodiments of the modular system, the anchor component is selected from an array in which each anchor component has a proximal portion having a proximal surface for contacting at least a portion of the coupler component and a distal portion for positioning within bone, the proximal portion having an angle of inclination of from about 120 to about 145 degrees and comprising a coupler component engagement feature.

Further, according to such embodiments, the humeral head prosthesis component includes on its engagement surface an engagement feature for concentric engagement with the coupler component. In use, each of the selected prosthesis, anchor and coupler components are engaged and the coupler and anchor components are recessed into bone, the arthroplasty assembly achieves alignment of the bone articulation surface of the humeral head prosthesis component with the bone that is anatomically similar to a native long bone.

Prior to fixation within the bone, the position of the humeral head prosthesis component can be varied rotationally around a shared central engagement axis with the coupler component to achieve the desired orientation of the elliptical humeral head relative to the humerus and the glenoid. And the position of the anchor component relative to the coupler component can be varied in two dimensions on a plane that is perpendicular to the central engagement axis of the coupler and humeral head prosthesis components by selecting the coupler component from an array comprising a plurality of coupler components that include variably positioned anchor engagement features.

In some embodiments comprising an anchor and coupler component, the anchor engagement component of the coupler component is radially offset from the central axis by from about 1 mm to about 20 mm. And, in some embodiments comprising an anchor and coupler component, the at least one anchor engagement feature of the disc shaped coupler component is radially offset from the central axis at a distance selected from one of about 1 mm to about 8 mm, and from about 1 mm to about 6 mm, and from about 1 mm to about 3 mm.

It will be appreciated that the coupler is in some embodiments adapted for use above the bone cut line, partially below the bone cut line, or as more particularly described and shown herein, countersunk essentially completely below the bone cut line. The advantages of the coupler as described herein can be realized in any implant configuration whether above, or partially or fully recessed below the bone cut line, particularly to enable customized selection and fit of implant components without being constrained by inventory limitations or by less than desirable implant height, neck angle, version, and posterior and medial offset.

In some embodiments, the use of the coupler with the elliptical heads enable surgical techniques wherein the coupler is completely or partially recessed within the humeral bone (i.e., below the cut line) to allow a greater range of options with respect to establishing the desired center of rotation in the shoulder joint. According to such embodiments, the elliptical head is engaged concentrically with the coupler.

The modular system enables achievement of a more anatomically accurate joint replacement aimed at reducing clinically adverse consequences. And the coupler with its eccentric taper enables a wider range of selection of humeral head orientation without compromise of height, neck angle, version, and posterior and medial offset. This offset function, together with the anatomical benefits thereby attained, finally solves a vexing challenge in the art. That is, provision for truly adaptable and convertible, anatomically accurate implants—a challenge that has been heretofore addressed, inadequately at best, with either expansive prosthetic humeral head inventory and/or adjustable systems that sacrifice one or more of the anatomically desirable implant features such as component height, neck angle, version, and posterior and medial offset.

It will be appreciated that the individual components of the prosthetic implants disclosed herein may be made using a variety of materials, including metal, ceramic and plastic and combinations of these. Such materials include but are not limited to: metals such as, for example, stainless steel, titanium alloys, cobalt alloys, cobalt chrome, superelastic metals, such as nitinol, polymers, such as polyester and polyethylene, polyether ether ketone (PEEK), carbon and carbon fiber materials. Porous coatings may be provided for any or a portion of the components, and specifically as described herein or as otherwise known in the art. The components may be provided with HA either dispersed on all or a portion of a surface, dispersed within all or a portion of the material of manufacture, and combinations of these.

Of course it will be appreciated by one of ordinary skill in the art that while this application is directed in its examples to the humerus and the glenohumeral joint, the application is not necessarily limited to the humerus and the principles, prosthesis systems and methods can be more generally applicable to arthroplasty for achieving native anatomy in the context of other bones.

EXAMPLES

Examination of Spherical Versus Elliptical Prosthetic Humeral Heads: A Comparison of Anatomical Fit: Quantifying the influence of prosthetic humeral head shape as well as the number of available prosthetic head sizes on replicating the normal humeral head anatomy during shoulder reconstructive surgery.

Methods:

Computer modeling software was used to create virtual sets of both spherically and elliptically shaped prosthetic heads, which were virtually implanted into three-dimensional CT-scan based models of 79 proximal humeri. Anatomical replication was considered successful if measured parameters (diameters of the base of the head in the frontal and sagittal planes, radii of curvature in the frontal and sagittal planes, and humeral head height) were all reproduced within 3 mm. The Fisher exact test was used to compare the percentage of successful replications for both head types, and to compare differences resulting from the use of sets with fewer or more available head sizes. Statistical significance was set at $P \leq 0.05$.

Much emphasis has been placed on replicating normal, prepathologic anatomy during shoulder reconstructive surgery. The underlying belief is that more accurate replication will lead to better functional outcomes. This notion is supported by recent biomechanical studies where it was found that rotational range of motion and glenohumeral joint kinematics were improved in vitro during shoulder reconstruction by employing a prosthetic humeral head with an anatomically accurate shape.

That the humeral head is ovoid in shape has been well documented, yet implantation of spherically shaped prosthetic heads during shoulder reconstructive surgery remains the norm. It has been reported that adverse effects on glenohumeral biomechanics might result if the size and position of the articular surface is altered by 4-5 mm during shoulder arthroplasty surgery. A potential concern based on this is that the mismatch often exceeds 4 mm when comparing normal anatomical measurements to that of a humerus that has been reconstructed with a spherically shaped prosthetic head.

Though it is generally accepted that the normal anatomy might not be perfectly replicated with use of spherical prosthetic heads, there has not been any study in which the anatomical fit of spherically versus elliptically shaped prosthetic heads has been quantified. More specifically, no study has directly compared the ability of both prosthetic head types to reproduce the normal anatomical relationships when implanted in multiple humeral specimens of various sizes.

The potential of two different types of prosthetic heads were evaluated for accurately replicating the normal, anatomical humeral head dimensions. The prosthetic head types studied included: 1) traditional, spherically shaped heads, and 2) elliptically shaped heads that conformed to dimensions that were described in a previous study. The primary goal of this study was to quantify the ability of each prosthetic head type to replicate the normal anatomy when applied to a bone database representing a sample of the population. Secondarily, we evaluated how increasing the number of available prosthetic head sizes per set might improve a set's ability to replicate the normal anatomy. We evaluated whether elliptically shaped heads would achieve replication of the normal anatomy in a higher percentage of cases compared to spherical heads, and that increasing the number of heads per set would enhance the ability of both head types to reproduce the normal anatomical relationships.

Evaluation Parameters:

De-identified three-dimensional (3D) CT-scan based models were obtained of 79 proximal humeri from Caucasian subjects from the United States and Australia (47 male and 32 female; ages, 17-87 years, with an average age of 56 years). The models were obtained from a second party (Materialise, Leuven, Belgium) and were prescreened to exclude specimens with osteophytes or other obvious degenerative changes. A detailed anthropometric analysis of the humeral models that were used for this study is documented in a previously published article.

Computer-aided design (CAD) software (SolidWorks 2014; Dassault Systèmes S.A., Waltham, Mass., USA) was employed to digitally model both spherically shaped and elliptically shaped prosthetic humeral heads. Anthropometric data shown in FIGS. 19-22 was considered when creating both spherical and elliptical prosthetic heads, with the goal of maximizing the number of humeral specimens for each head type in which a good fit could be achieved. The humeral head dimensional formulae were applied directly when creating the elliptical prosthetic heads. Referring again to FIG. 2, the measured parameters for both head types included the diameters at the base of the head in both the frontal (DF) and sagittal (DS) planes, the radii of curvature in both the frontal (ROCF) and sagittal (ROCS) planes, and humeral head height (HHH). Four sets of prosthetic heads of each head type were created such that each set included heads that increased in size from small to large in 4, 3, 2, or 1 mm increments. The values for the smallest and largest heads (DF≥40 mm, and DF≤56 mm, respectively) were selected to cover the range of humeral head sizes based on the anthropometric data. The number of heads per set was determined by the value by which the head size was incrementally increased: starting at 40 mm, a 4 mm incremental increase in head size based on DF resulted in a set with 5 heads (Set A), a 3 mm incremental increase produced a set with 6 heads (Set B), a 2 mm increase yielded 9 heads (Set C), and a 1 mm increase produced a set with 17 heads (Set D). The parameter measurements of the head types and sizes are provided in Table I, FIG. 16.

Prosthetic heads from each set were virtually implanted into each of the 79 humeral models. The number of humeri within the study population whose anatomy could or could not be replicated within 3 mm was recorded for each set of prosthetic heads, and percentages were calculated. For any given specimen, every one of the measured parameters (DF, DS, ROCF, ROCS, and HHH) had to be reproduced within 3 mm of the native anatomy in order for the replication to be considered successful. Contingency tables (2×2) were created, and the Fisher exact test was used to determine statistical significance when comparing the percentages of successful replication for each of the different sets of prosthetic heads (GraphPad Software, QuickCalcs; La Jolla, Calif., USA). The method of summing small P values was used to compute two-tailed P values. Statistical significance was set at P≤0.05. The null hypotheses for the Fisher exact tests were that: 1) there would be no difference between sets of spherical versus elliptical heads in their ability to replicate the normal anatomy within 3 mm, and 2) increasing the number of available head sizes per set would not improve a set's ability to replicate the normal anatomy.

A power calculator (G*Power 3, Version 3.1.9.2 for Mac OsX; Dusseldorf, Germany) was used to perform a post hoc power analysis. Statistical power of 0.8 or higher was considered adequate. In cases where the power was found to be inadequate, an a priori power analysis was performed using the known proportions to determine the minimum sample size that would be needed to adequately power future studies. The a priori power analyses were performed under the assumption of an α error probability of 0.05, an allocation sample size ratio (N2/N1) of 1, and a power (1-β error probability) of 0.8.

The findings were then evaluated to identify which of the parameters (DS, ROCF, ROCS, and HHH) most frequently prevented successful replication of the normal anatomy. The individual parameters that prevented the normal anatomy from being successfully replicated within 3 mm were tallied and recorded for each set of heads. Referring again to the drawings, complete results are listed in Tables II and III, corresponding with FIGS. 17 and 18. When comparing sets with equal numbers of either spherical or elliptical prosthetic heads (Table II, Comparison Group 1), the sets with elliptical heads provided the ability to replicate the anatomy in a higher percentage of humeral specimens in each case (P≤0.0001).

When comparing a set of elliptical heads with only 5 heads per set to sets of spherical heads with either 5, 6, 9, or 17 heads (Table II, Comparison Group 2), the set with 5 elliptical heads was able to replicate the anatomy in a higher percentage of patients in each case (96% versus 41%, 66%, 71%, and 78% respectively), and the differences were found to be statistically significant in each case (P≤0.0013).

The hypothesis that increasing the number of prosthetic heads per set would enhance anatomical replication of the normal humeral head parameters was substantiated for sets of spherical heads, but not for sets of elliptical heads. Increasing the number of available spherical head sizes from 5 to 6, 9 or 17 heads per set improved the ability to replicate the normal anatomy from 41% to 66%, 71% and 78% respectively (P≤0.0023). A trend of improved replication was seen when increasing the number of available head sizes from 6 to 9 or 17, but the sample sizes in this study (N1=79; N2=79) were too small to determine whether this was statistically significant (Table II, Comparison Group 3).

With use of elliptical prosthetic heads, the normal anatomy could be replicated within 3 mm in 96% of the specimens with 5 heads per set, 99% with 6 heads, 99% with 9 heads, and 100% with 17 heads (Table II, Comparison Group 1). No statistically significant improvement in replication was found when increasing the number of available elliptical head sizes above 5 per set (P≥0.2452), and the sample sizes (N1=79; N2=79) were too small to detect any potential differences that might exist by increasing the number of elliptical heads above 5 per set (Table II, Comparison Group 4).

When the parameters that prevented replication of the normal anatomy within 3 mm for each humeral specimen were tallied, DS was by far the most influential parameter (Table III). The next most influential parameter was ROCS, followed by ROCF. Humeral head height could be replicated within 3 mm for 100% of the specimens regardless of head type or the number of heads per set.

Discussion:

Many authors have previously noted that the normal, anatomical shape of the humeral head is not spherical. Others have reported that the use of a spherical prosthetic humeral head will result in imprecise restoration of the native geometry and improper placement of the center of rotation in comparison to the native head. In this in silico study, the results of anatomical reconstruction with spherical versus elliptical prosthetic heads were compared and quantified across a sample population, and the results confirmed the hypothesis that use of elliptical prosthetic humeral heads would better replicate the normal humeral head shape. Simultaneous replication of the diameters of the base of the head in both the frontal (DF) and the sagittal (DS) planes could not be achieved within 3 mm in many cases when spherical heads were employed (Table III). When all parameters (DF, DS, ROCF, ROCS, and HHH) were considered, it was possible to replicate the normal anatomy within 3 mm in a higher percentage of specimens using elliptical (96-100%) as opposed to spherical (41-78%) prosthetic heads ($P \leq 0.0013$) (Table II, Comparison groups 1 and 2).

We have shown that successful replication of the humeral head anatomy could be achieved for most patients with an inventory of only 5 or 6 prosthetic elliptical humeral heads.

Background in the Technical Field:

It will be appreciated that whether or not an implant is anatomically correct, some implants in the art are designed to be usable in either a standard to a reverse configuration. Typically, within the art, convertible implants allow the surgeon to convert by removing the standard prosthetic head from the stem and replacing the head with a cup (to mimic the glenoid) (examples within the art include convertible shoulder arthroplasty systems by Biomet, Zimmer, Tornier, Exactech). With such prostheses, the cup sits on top of the bone cut rather than being recessed within the bone. A disadvantage of this technique and prosthesis design is that the humerus becomes overlengthened or distalized, predisposing the patient to nerve stretch injury, joint stiffness, and acromial fracture. Thus, while these convertible systems offer the benefit of a less invasive reoperation, the tradeoff is increased risk of surgical complications and inferior biomechanical outcomes, all of which are due to the increased height of the implant that result from placement of the cup above the bone cut. This is particularly true with respect to reverse shoulder revisions when compared to primary reverse shoulder arthroplasty that is achieved with a reverse-specific implant where the cup is recessed into the proximal humerus bone (examples within the art of primary reverse shoulder arthroplasty systems include those by DJO Surgical, DePuy, and Tornier). Arm lengthening, nerve palsies, joint instability, impingement, joint stiffness, acromial fractures, and difficulty with prosthesis conversion that ultimately leads to stem extraction and bone fracture are all examples of undesirable clinical outcomes resulting from current convertible and primary arthroplasty systems.

Most reverse shoulder arthroplasty systems are designed to deliberately shift the rotational center of the joint in order to take what is believed to be best advantage of the remaining musculature by tensioning the deltoid to compensate for loss of rotator cuff function. The approach yields a distal shift of the arm/humerus (i.e., towards the direction of the patient's feet). This distal shift is achieved through an increase in the overall length of the humerus through the height of the implant beyond the cut line of the humeral head. While there are perceived advantages to this approach, known problems that come with increased distalization of the arm include 1) acromial/scapular fracture, and 2) nerve injury from the stretch on the nerves. Indeed, while some experts may tout the advantages of increasing deltoid tension, others report that " . . . an increase in passive tension of the deltoid on the acromion, can lead to fatigue, stress, or complete fracture [Hamid N, et al. Acromial Fracture After Reverse Shoulder Arthroplasty. Am J Orthop. 2011.40(7): E125-E129]. Werner et al reported a 7.3 incidence of scapular fracture in revision cases, and a 6.3% incidence during primary arthroplasty [Werner C M, et al. Treatment of painful pseudo-paresis due to irreparable rotator cuff dysfunction with the Delta III reverse-ball-and-socket total shoulder prosthesis. J Bone Joint Surg Am. 2005.87:1476-86]. Others have reported a 7.7% incidence of neuropraxia during revision reverse shoulder arthroplasty [Total Reverse Shoulder Arthroplasty: European Lessons and Future Trends. Seebauer L. Am J Orthop. 2007.36(12 Supplement): 22-28.]. The high incidence of nerve injury is probably due to the stretch on the brachial plexus nerves that occurs as the humerus is lengthened. Especially in patients with stiff, contracted shoulders, it is not advisable to over-lengthen the arm. In view of these undesirable clinical effects that derive from the mechanical lengthening of the bone, there is a need to provide an arthroplasty system that is specifically designed to avoid distalization.

Yet another challenge in the art is the absence of anatomically correct head articulation surfaces. It is known that the native anatomical shape of the humeral head is not spherical, but elliptical (i.e., where the cross section of the humeral head has a radius of curvature in the superior to inferior dimension that is greater than the radius of curvature of the cross section in the anterior to posterior dimension). Recent research has shown that a prosthetic humeral head having a cross sectional shape adjacent to the bone cut that is elliptically-shaped and a generally spherical center point would theoretically allow a patient to have improved shoulder range of motion and function postoperatively. However, because the center of rotation of the humeral head is offset from the long axis of the humeral bone, it has been impractical for any shoulder implant company to create a prosthesis with an elliptically-shaped prosthetic humeral head. Merely coupling an elliptically-shaped head with a traditional stemmed prosthesis design would present difficulties accounting for the surgeon's need to simultaneously achieve the proper head size, correct rotational orientation of the elliptical head, and the proper amount of superior to inferior and anterior to posterior offset relative to the stem.

Moreover, in many shoulder surgeries, only the humeral portion of the joint is replaced while the native glenoid is left intact, presenting a challenge of matching the articulating surface of the head prosthetic with the native articulating surface of the glenoid. This challenge is not present in total arthroplasty, where both the humeral and the glenoid portions are replaced with prosthetics. Ideally, a shoulder arthroplasty system would provide a wide range of head choices and offsets to most precisely match the patient's native anatomy. With such a system, a near perfect match could be achieved in a hemi-arthroplasty, and in if the system were modular, could be adapted in a revision to provide an ideal match if the shoulder is converted to either a total arthroplasty or to a reverse shoulder arthroplasty. The current art does not provide such modular systems, thus, to accomplish the desirable offsets with traditional stem designs, whether using spherical or elliptical heads, it would be necessary to stock an essentially infinite inventory of prosthetic heads and/or stems with variable offsets for achieving the desired shape, size and positioning, which is, of course, economically impractical.

Another challenge in joint replacement is the general requirement for complete implant removal in the instance where a corrective or revision surgery is needed with a primary arthroplasty system. A common feature among the shoulder arthroplasty devices in the art is that they are typically designed for a single use, and typically cannot be repurposed in a later surgery on the same patient. Thus, any post implantation procedure which the patient may require due to further bone or soft tissue deterioration, such as a revision or conversion to a reverse configuration, typically requires a bony procedure wherein all or a portion of the implanted prosthesis must be removed from bone in order to allow implantation of a new device. It is well known that in a percentage of initial shoulder arthroplasty cases, the patient will require revision surgery due to device failure, infection, or further degeneration of the bone or soft tissues of the joint. In some specific situations, the revision will require conversion of the humeral side of the joint from a standard implant to a reverse implant. It is desirable, though typically not possible, to avoid any bony procedure during revision cases because there is a high risk of humeral fracture and/or bony destruction when the surgeon attempts to remove a well-fixed humeral component from the humerus. It is desirable to advance the art with devices that achieve structural stability of an implant within the bone while retaining the ability to remove the device without bone fracture or catastrophic loss of bone during removal.

The objective of implant stability is addressed, in the context of long bones, through implant length, proximal diameter, and material selection and surface treatment that can enhance bony ingrowth on the implant. In the art of shoulder arthroplasty, there are a variety of short-stemmed and stemless devices that have implant surface features that encourage bony ingrowth and implant dimensions that are intended to achieve stability. While these features are helpful to encourage securement within bone, they are developed based on averages within a broad patient population, for example in terms of proximal humerus head and diaphysis dimensions and contribute to some of the other challenges of arthroplasty in that they provide only a limited range of possible device configurations and features for achieving bony fixation.

And it is a well-known problem that removal of a prosthesis component that is well fixed in the bone is made more difficult when the structural features of implant components limit the surgeon's ability to apply surgical instruments such as an osteotome to free the prosthesis from the bone, especially in the metaphyseal and diaphyseal regions. It is the very structural elements that provide the opportunity for enhanced fixation that also lead to significant bone damage and loss in the likely event that a revision is needed. The art presently lacks arthroplasty implants with features that enable achievement of bony fixation and enable removal of components for revision to minimize bone loss while enabling the repurposing of the primary implants for alternate use.

A need exists to provide a humeral prosthesis that is designed to be modular and adaptable to enable a closer approximation of native anatomical fit for a broader range of patients rather than a patient population. Further, there is a need for a device that mitigates the problems associated with height position of a prosthesis in the humerus bone at the time of the index procedure and/or a revision surgery so that distalization of the humerus is avoided if conversion to a reverse shoulder arthroplasty is required. And there is a need for devices that are optimized for proximal bony ingrowth and distal (diaphyseal) stability to achieve short and long-term device stability while retaining the ability to revise and possibly remove the implant without catastrophic bone effects.

While some devices and device features exist within the art that are designed to protect against humeral bone loss in revision surgeries, there remains a need for a system that enables replacement or conversion of a humeral prosthesis without the requirement for bony procedure or at least minimal need for removal of implant from within the bone.

To address needs in the art, including the several needs identified, this disclosure provides a system that is modular and convertible and optimized achieve closer approximation of a patient's native anatomy, including avoidance of arm distalization, avoidance of surgery-related bone loss, while enabling a wider range of options for matching anatomy on during the index procedure as well as during surgical revision.

This disclosure describes exemplary embodiments in accordance with the general inventive concepts and is not intended to limit the scope of the invention in any way. Indeed, the invention as described in the specification is broader than and unlimited by the exemplary embodiments and examples set forth herein, and the terms used herein have their full ordinary meaning.

The general inventive concepts are described with occasional reference to the exemplary embodiments and the exemplary embodiments depicted in the drawings. Unless otherwise defined, all technical and scientific terms used herein have the same meaning as commonly understood by one of ordinary skill in the art encompassing the general inventive concepts. The terminology set forth in this detailed description is for describing particular embodiments only and is not intended to be limiting of the general inventive concepts.

To the extent used herein, the singular forms "a," "an," and "the" are intended to include the plural forms as well, unless the context clearly indicates otherwise. The term "proximal" to the extent used herein in connection with any object refers to the portion of the object that is closest to the operator of the object (or some other stated reference point), and to the extent used herein, the term "distal" refers to the portion of the object that is farthest from the operator of the object (or some other stated reference point). The terms "surgeon" and "operator" to the extent used herein are used interchangeably herein and each is intended to mean and refer to any professional or paraprofessional who delivers clinical care to a medical patient, particularly in connection with the delivery of care, including but not limited to a surgeon. Likewise, the terms "patient" and "subject" to the extent used herein are used interchangeably herein and each is intended to mean and refer to any clinical animal subject, including a human medical patient, particularly in connection with the delivery of care thereto by anyone, including a surgeon or operator to the extent those terms are used herein.

Spatially relative terms, such as "inner," "outer," "beneath", "below", "lower", "above", "upper" and the like, to the extent used herein, may be used herein for ease of description to describe one element or feature's relationship to another element(s) or feature(s) as illustrated in the drawings. Spatially relative terms may be intended to encompass different orientations of the device in use or operation in addition to the orientation depicted in the drawings. For example, if the device in the drawings is turned over, elements described as "below" or "beneath" other elements or features would then be oriented "above" the other elements or features. Thus, the example term "below" can encompass both an orientation of above and below. Thus, an item may be otherwise oriented (rotated 90 degrees or at other orientations) and the spatially relative descriptors used herein interpreted accordingly. With respect to any references to the extent used herein that may be made relative to an object, or to a body or subject for example that of a human patient, the terms "cephalad," "cranial" and "superior" indicate a direction toward the head, and the terms "caudad" and "inferior" and "distal" indicate a direction toward the feet. Likewise, the terms "dorsal" and "posterior" indicate a direction toward the back, and the terms "ventral" and "anterior" indicate a direction toward the front. And further, the term "lateral" indicates a direction toward a side of the body, the term "medial" indicates a direction toward the mid line of the body, and away from the side, the term "ipsalateral" indicates a direction toward a side that is proximal to the operator or the object being referenced, and the term "contralateral" indicates a direction toward a side that is distal to the operator or the object being referenced. More generally, any and all terms to the extent used herein providing spatial references to anatomical features shall have meaning that is customary in the art. And the terms "frontal" and "sagittal" have the meanings as ordinarily understood in the art with reference to a body, or body part, such as for example the shoulder.

Unless otherwise indicated, all numbers expressing quantities, properties, and so forth as used in the specification, drawings and claims are to be understood as being modified in all instances by the term "about." Accordingly, unless otherwise indicated, the numerical properties set forth in the specification and claims are approximations that may vary depending on the suitable properties desired in embodiments of the disclosure. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

While the disclosed embodiments have been described and depicted in the drawings in the context of the human shoulder, it should be understood by one of ordinary skill that all or various aspects of the embodiments hereof may be used in connection with other species and within any species in any joint in the body.

While various inventive aspects, concepts and features of the general inventive concepts are described and illustrated herein in the context of various exemplary embodiments, these various aspects, concepts and features may be used in many alternative embodiments, either individually or in various combinations and sub-combinations thereof. Unless expressly excluded herein all such combinations and sub-combinations are intended to be within the scope of the general inventive concepts. Still further, while various alternative embodiments as to the various aspects, concepts and features of the inventions (such as alternative materials, structures, configurations, methods, devices and components, alternatives as to form, fit and function, and so on) may be described herein, such descriptions are not intended to be a complete or exhaustive list of available alternative embodiments, whether presently known or later developed.

Those skilled in the art may readily adopt one or more of the inventive aspects, concepts, or features into additional embodiments and uses within the scope of the general inventive concepts, even if such embodiments are not expressly disclosed herein. Additionally, even though some features, concepts and aspects of the inventions may be described herein as being a preferred arrangement or method, such description is not intended to suggest that such feature is required or necessary unless expressly so stated. Still further, exemplary, or representative values and ranges may be included to assist in understanding the present disclosure. However, such values and ranges are not to be construed in a limiting sense and are intended to be critical values or ranges only if so expressly stated.

Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated.

What I claim:

1. A system for long bone arthroplasty comprising: an array of humeral head prosthesis components, each humeral head prosthesis component in the array having a convex articulation surface that is hemielliptical and is defined by a major axis (corresponding to a frontal plane) and a minor axis (corresponding to a sagittal plane), a major diameter (DF) along the major axis and a minor diameter (DS) along the minor axis, and radii of curvature along the major axis (ROCF) and along the minor axis (ROCS), each prosthesis component comprising an apex and a base each having an elliptical cross sectional shape, the array comprising a plurality of humeral head prosthesis components that (i) vary from one another in their major diameters in a range from about 1 to 4 mm, and (ii) vary from one another in at least one of minor diameter, humeral head height (HHH), ROCF and ROCS as a function of DF.

2. A system for long bone arthroplasty according to claim 1, wherein the plurality of humeral head prosthesis components that vary from one another are characterized as varying from having a base with a more circular cross-sectional shape to a more elongated elliptical cross-sectional shape with increasing DF.

3. A system for long bone arthroplasty according to claim 1, wherein DF varies across the plurality of humeral head prostheses in the range from about 40 mm to about 56 mm.

4. A system for long bone arthroplasty according to claim 3, wherein DF varies across the plurality of humeral head prostheses in the range from at least 40 mm to no more than 56 mm.

5. A system for long bone arthroplasty according to claim 1, wherein the array of elliptical humeral head prosthesis components provides for anatomical fit relative to a native humeral head within a variation of up to and not more than 3 mm in one or both of the DF and DS dimensions in at least 96% and up to 99% of a patient population in which a native humeral head has a minor diameter that is equal to 0.69 times a major diameter plus an additional length in millimeters of 10.8 millimeters plus or minus 1 or 2 millimeters.

6. A system for long bone arthroplasty comprising according to claim 1, wherein the plurality of humeral head prosthesis components is selected from the group of (i) an array of 5 heads that vary from one another in the major diameter in 4 mm increments, (ii) an array of 6 heads that vary from one another in the major diameter in 3 mm increments, (iii) an array of 9 heads that vary from one another in the major diameter in 2 mm increments, and (iv) an array of an array of 17 heads that vary from one another in the major diameter in 1 mm increments.

7. A system for long bone arthroplasty according to claim 6, wherein DF varies across the plurality of humeral head prostheses in the range from about 40 mm to about 56 mm.

8. A system for long bone arthroplasty according to claim 7, wherein DF varies across the plurality of humeral head prostheses in the range from at least 40 mm to no more than 56 mm.

9. A system for long bone arthroplasty according to claim 1, wherein an anatomical fit of a humeral head prosthesis component selected from the array is achieved by selecting a head based on size and by rotationally varying orientation of the selected head as compared with a native humeral head to most closely match a native anatomy of the native humeral head.

10. A system for long bone arthroplasty according to claim 1, further comprising at least one generally disc shaped coupler component having a central axis, a prosthesis component side comprising a recess configured to interface with and engage the humeral head prosthesis component, the recess having a substantially planar floor and a sidewall and at least one prosthesis component engagement feature, an opposing side having a bone contact surface, and a lateral edge that bounds the prosthesis component and opposing sides.

11. A system for long bone arthroplasty according to claim 10, wherein upon implanting into a long bone, an orientation of the major and minor axes of the humeral head prosthesis component relative to a center axis of the long bone is determined at the coupler-prosthesis interface.

12. A system for long bone arthroplasty according to claim 10, wherein the prosthesis component side of the coupler component is configured to interchangeably interface with and engage both a convex humeral head prosthesis component and a concave prosthesis component, the system further comprising a non-elliptical prosthesis component selected from one or more of (i) at least one concave cup having a cross sectional shape that is circular, and (ii) a convex head having a cross sectional shape that is circular.

13. A system for long bone arthroplasty according to claim 10, the coupler component comprising on the opposing side one or more of (i) a male taper, (ii) an anchor that is unitary with the coupler component and selected from a cage and a stem, and (iii) an anchor engagement feature extending from a surface and radially offset from the central axis.

14. A system for long bone arthroplasty according to claim 13, wherein the coupler component comprises on its opposing side at least one anchor engagement feature extending from a surface and radially offset from the central axis, the system further comprising an anchor component comprising a proximal portion having a proximal surface for contacting at least a portion of the opposing side of the coupler component and a distal portion for positioning within a bone, the proximal portion comprising on its proximal surface a coupler component engagement feature.

15. An arthroplasty assembly comprising:
a prosthesis component and a coupler component engageable to provide an arthroplasty assembly, wherein the position of the prosthesis component can be varied rotationally around a shared central engagement axis with the coupler component,
the prosthesis component selected from an array comprising a plurality of humeral head prosthesis components that (i) vary from one another in their major diameters in a range from about 1 to 4 mm, and (ii) vary from one another in at least one of minor diameter, humeral head height (HHH), ROCF and ROCS as a function of DF, wherein each humeral head prosthesis component in the array has a convex articulation surface that is hemielliptical and is defined by a major axis (corresponding to a frontal plane) and a minor axis (corresponding to a sagittal plane), a major diameter (DF) along the major axis and a minor diameter (DS) along the minor axis, and radii of curvature along the major axis (ROCF) and along the minor axis (ROCS), each prosthesis component comprising an apex and a base each having an elliptical cross sectional shape
the coupler component comprising a prosthesis component engagement side and an opposite side comprising a bone contact surface, the sides bounded by a lateral edge that is one of cylindrical, frustoconical and frustohemispherical,
wherein, when one of the selected prosthesis and coupler components are engaged and the coupler component is recessed into bone, rotation of the prosthesis component within the coupler component provides alignment of the bone articulation surface of the prosthesis component with the bone that is anatomically similar to a native long bone.

16. An arthroplasty assembly according to claim 15, wherein the assembly is anchorless.

17. An arthroplasty assembly according to claim 15, wherein the assembly comprises an anchor component, and wherein the coupler component is selected from an array that includes a plurality of coupler components, each coupler component in the array comprising on its opposing side a variably positioned anchor engagement feature, wherein each of at least two of the plurality of coupler components comprises at least one anchor engagement feature that is off-center from a center point of the coupler component, and wherein the off-center engagement feature on each of the at least two coupler components is at a different distance in at least one dimension relative to the center point, and wherein the anchor component is selected from an array that includes a plurality of anchor components each comprising a proximal portion having a proximal surface for contacting at least a portion of the coupler component and a distal portion for positioning within bone, the proximal portion having an angle of inclination of from about 120 to about 145 degrees relative to a long bone, and comprising a coupler component engagement feature.

18. A method for implanting a modular system for long bone arthroplasty comprising:
(a) providing an arthroplasty assembly according to claim 15;
(b) selecting the coupler component and one prosthesis component;
(c) at least provisionally fitting the selected coupler component into a metaphysis of a long bone; and
(d) engaging the selected prosthesis component into the recess of the prosthesis component side of the coupler component.

19. The method for implanting a modular system for long bone arthroplasty according to claim 18, wherein the coupler component comprises on the opposing side, one or more of a male taper, an anchor that is unitary with the coupler component and selected from a cage and a stem, and an anchor engagement feature extending from a surface and radially offset from the central axis.

20. The method for implanting a modular system for long bone arthroplasty according to claim 19, comprising:
on the opposing side of the coupler component at least one anchor engagement feature extending from the bone contact surface and radially offset from the central axis, and an anchor component comprising a proximal portion having a proximal surface for contacting at least a portion of the anchor component side of the coupler component and a distal portion for positioning within a bone, the proximal portion comprising on its proximal surface a coupler component engagement feature, wherein an orientation of the major and minor axes of the humeral head prosthesis component relative to a center axis of the long bone is determined at the coupler-prosthesis interface, and wherein an offset of the prosthesis component from the center axis of the long bone is determined at the anchor-coupler interface.

\* \* \* \* \*